US009518928B2

(12) United States Patent
Steinbrueck et al.

(10) Patent No.: US 9,518,928 B2
(45) Date of Patent: Dec. 13, 2016

(54) OPTODE FOR DETERMINING CHEMICAL PARAMETERS

(71) Applicants: Doerte Steinbrueck, Potsdam (DE); Elmar Schmaelzlin, Potsdam (DE); Hans-Gerd Loehmannsroeben, Wolfsburg (DE)

(72) Inventors: Doerte Steinbrueck, Potsdam (DE); Elmar Schmaelzlin, Potsdam (DE); Hans-Gerd Loehmannsroeben, Wolfsburg (DE)

(73) Assignee: UNIVERSITAET POTSDAM, Potsdam (DE)

( * ) Notice: Subject to any disclaimer, the term of this patent is extended or adjusted under 35 U.S.C. 154(b) by 24 days.

(21) Appl. No.: 14/373,397

(22) PCT Filed: Jan. 18, 2013

(86) PCT No.: PCT/EP2013/050991
§ 371 (c)(1),
(2) Date: Jul. 21, 2014

(87) PCT Pub. No.: WO2013/107895
PCT Pub. Date: Jul. 25, 2013

(65) Prior Publication Data
US 2015/0011010 A1    Jan. 8, 2015

(30) Foreign Application Priority Data

Jan. 19, 2012   (EP) ..................................... 12151830

(51) Int. Cl.
*G01N 31/16*  (2006.01)
*G01N 21/80*  (2006.01)
*G01N 21/64*  (2006.01)

(52) U.S. Cl.
CPC ............ *G01N 21/80* (2013.01); *G01N 21/643* (2013.01); *G01N 21/6408* (2013.01); *G01N 21/6428* (2013.01); *G01N 2021/6434* (2013.01); *G01N 2021/6439* (2013.01); *G01N 2201/0612* (2013.01); *G01N 2201/08* (2013.01)

(58) Field of Classification Search
None
See application file for complete search history.

(56) References Cited

U.S. PATENT DOCUMENTS

2008/0286154 A1    11/2008 Kane

FOREIGN PATENT DOCUMENTS

| WO | 9417388 A1 | 8/1994 |
| WO | 0175450 A2 | 10/2001 |
| WO | 02066162 A1 | 8/2002 |

OTHER PUBLICATIONS

Hille et al., "Time-domain fluorescence lifetime imaging for intracellular pH sensing in living tissues," Anal. Bioanal. Chem., 391:1871-1879 (2008).

*Primary Examiner* — Robert Xu
(74) *Attorney, Agent, or Firm* — Kriegsman & Kriegsman

(57) ABSTRACT

The invention is related to an optode for determining chemical parameters of a sample wherein the optode consists of a polymer matrix consisting of sulfonated polyether ether ketone (SPEEK) in which a sensor dye is immobilized or more than one sensor dye is immobilized, wherein at least one of the immobilized sensor dyes is pH-sensitive.
In addition, the present invention also concerns a method for determining the pH of a sample in which the invention-related optode is used.

18 Claims, 17 Drawing Sheets

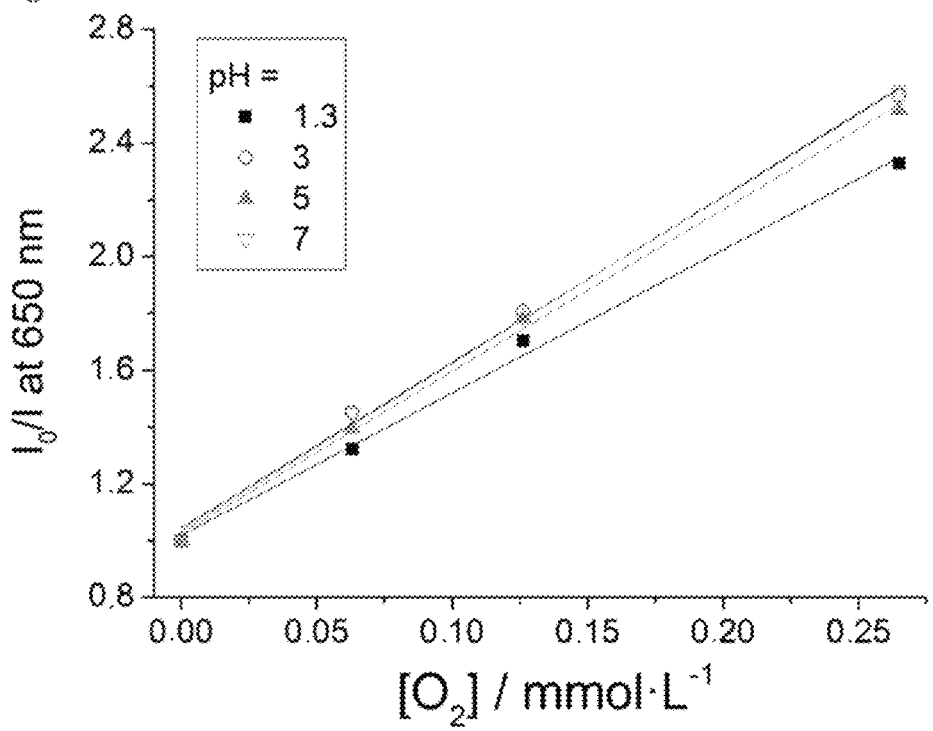
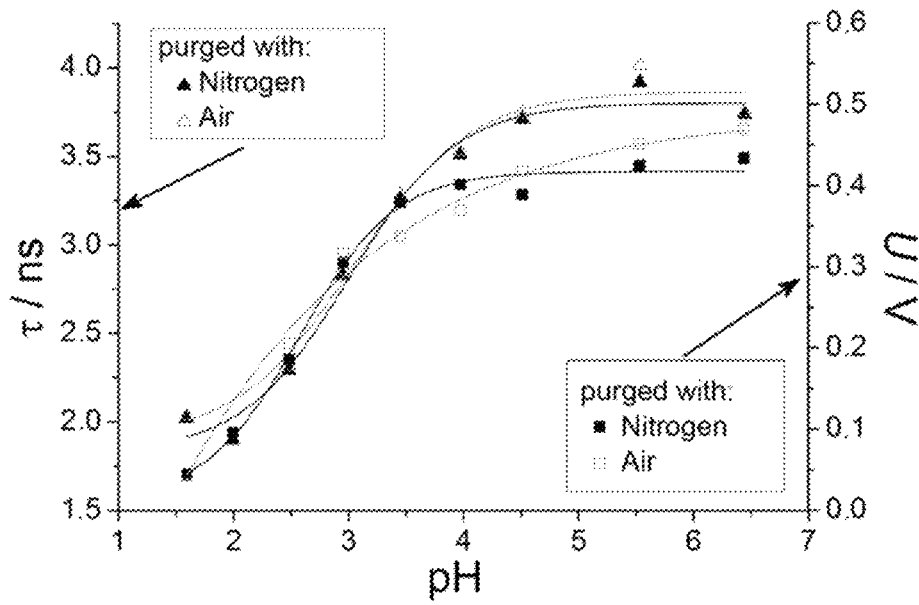

OPTODE FOR DETERMINING CHEMICAL PARAMETERS

Subject of the present invention is an optode for determining the chemical parameters of a sensor as well as a method for determining chemical parameters using the optode in accordance with this invention.

Chemical parameters in the context of this invention are understood to be pH value and the concentration of substances.

Chemical sensors are components which provide an analytically evaluable signal from chemical information.

Optodes are probes which demonstrate visually the presence of chemical substances or indicate chemical parameters with the aid of a sensor dye. As a proof, the use is made of the fact that the optical properties of sensor dyes, for example their luminescence, change in the presence of the substance to be detected or its chemical parameters. Especially well-known are optodes with which the sensor dye is directly fixed to, or in a matrix on, an optical fiber.

The determination of chemical parameters such as pH and the concentrations of oxygen, carbon dioxide, ammonia, metal ions such as those of sodium, potassium and calcium in a sample is of great importance in many areas. The concentration of oxygen in nature is decisive in the development of life and plays an important role in many biological processes. The pH is critical in the functioning of enzymes and receptors and so in many physiological processes, such as the conducting of signals along nerve cells and the ability to absorb oxygen or carbon dioxide in the tissues or blood of plants and animals. These chemical parameters therefore govern the health and activity of living creatures. Furthermore, the parameters provide information on the corrosive strength of solutions, e.g. in technical plants, and so influence running processes and the stability of materials. Fast, uncomplicated and reliable analytical methods are therefore required for diverse applications.

The spectrum of possible areas of application ranges from determining conditions in individual cells via foodstuff and bioreactor monitoring to supervision of underground and process plants, e.g. geothermal or crude oil drilling.

The immense potential of optical methods for miniaturization in biological applications is significant. The use of optical fiber cables is a great advantage in technical applications where great distances are involved, sometimes kilometers, between the measuring station and the actual sample.

The use of optodes is already state-of-the-art in determining pH and other chemical parameters such as oxygen concentration. Optodes have already been described that allow the determination of several chemical parameters. In evaluating the suitability of optodes for implementation, the optical measurement method most suited to optodes must be taken into consideration. In this, a differentiation has to be made as to whether the optodes are suitable for both stationary and time-resolved optical methods.

Stationary methods can be used to determine the change in luminescence intensity of a sensor dye as a function of the change in analytic concentration. For this, the sensor dyes are excited as far as possible at the maximum of the absorption bands and emission spectra for different analytical concentrations. The evaluation of the luminous intensity at certain emission wavelengths results in a function which is dependent on the concentration of the analyte.

In the time-resolved methods (time domain spectroscopy; TD-S), a further specific property of the dye is determined—the decay time.

The decay time is the time taken by the luminescence intensity to fall to a given percentage of its original value. The term "luminescence" will be used in the context of the present invention as a blanket term for fluorescence and phosphorescence.

A great advantage of the decay time determination is that it is largely independent of the dye concentration within the sensor matrix and of fluctuations in the intensity of the excitation source. Time-resolved methods also supply, in addition to the stationary intensity change, the time-dependent absorption of the luminescence intensity after excitation by a short light pulse.

Phase-modulation spectroscopy is one of the methods in which the decay time of a sensor dye is determined. This allows real-time measurements due to the fast response times of the sensors ($\leq 10$ s) and a fast measurement technique. Also, very small signal intensities suffice without this having an effect on the accuracy of the measurement.

The optical determination of chemical parameters has established itself over the last 30 years. The first scientific article on optical fiber pH measurement appeared in 1980 (S. R. Goldstein, J. Peterson, R. V. Fitzgerald, A miniature fiber optic pH sensor for physiological use, Journal of Biomechanical Engineering 1980, 102 (2), 141-146). The first commercial fiber optic systems for the determination of the chemical parameters pH or oxygen concentration became available in 1992 (Ocean Optics), and others followed: Sentronic (1993), Presens (1997), Pyro Science and Colibri Photonics (2011).

In addition to determining a single chemical parameter, the determination of two or more parameters is also desirable in various areas. The particular case of simultaneous determination of several chemical parameters is of great interest. The possibility of determining several parameters using one measurement makes the analytics not only more cost effective but also faster. Also, less material is required in the sample, which is important—especially in medical applications.

State-of-the-art optodes are already known for the determination of several chemical parameters. For example, N. B. Borchert, G. V. Ponomarev, J. P. Kerry and D. B. Papkovsky, in "$O_2$/pH multisensor based on one phosphorescent dye", Anal. Chem. 2011, 83, 18-22, describe the simultaneous measurement of oxygen and pH using an optode. The optode described in the publication consists of a metalloporphyrin dye embedded in a polymer membrane. This sensor dye was functionalized in such a way that it could be used for the determination of oxygen content and for pH. This bifunctional sensor dye is integrated into a matrix of polyvinylchloride and bis-(2-ethylhexyl)sebacate. In this publication, a discussion takes place about the use of more than one sensor dye in a sensor possibly leading to interactions and an overlapping of the suitable spectral ranges. Reference is also made to the high manufacturing costs of optodes which contain several sensor dyes. No mention is made that the pH value with the disclosed optode is determined, or can be determined, by means of the decay time of the sensor dye. The multioptodes described by Borchert et al. enable the measurement of pH in the range 5 to 9. The measurement of lower pH values is nor revealed.

An optode, which can determine pH and, after the attachment of a further matrix, is also suitable for determining concentrations of carbon dioxide and ammonia, is described by Nivens et al. (D. A. Nivens et al., "Multilayer sol-gel membranes for optical sensing applications: single layer pH and dual layer $CO_2$ and $NH_3$ sensors", Talanta 2002, 58, 543-550.

The measurements of pH and concentrations of $CO_2$ and $NH_3$ only take place after the sensor has been modified. A sensor for measuring pH is used which includes a base-catalyzed sol-gel into which the indicator hydroxypyrene trisulfonic acid has been introduced. This sensor can be used to determine the pH value. If $CO_2$ or $NH_3$ concentrations are to be measured with this sensor, a further layer is applied on top of the sol-gel layer of the pH sensor, the latter being a hydrophobic sol-gel layer. This is to prevent interactions. A simultaneous determination of several chemical parameter is not revealed in the publication named. The measurement of the luminescence decay time of the pH-sensitive dye is also not revealed.

On the whole, the inventors have discovered that state-of-the-art pH-sensitive optodes can be based on the measurement of pH-dependent, stationary fluorescence intensity (see: J. Lin, "Recent development and applications of optical and fiber-optic pH sensors", Trends in analytical chemistry 2000, 19, 541-551). No optical probe is described as state-of-the-art, which consists of a pH-sensitive dye, immobilized in a matrix and which enables a pH measurement via determination of the luminescence decay time of the pH-sensitive dye.

The direct measurement of the pH via the decay time of a pH-sensitive dye has only been demonstrated up to now with dissolved dyes (C. Hille et al., "Time-domain fluorescence lifetime imaging for intracellular pH sensing in living tissues"; H.-J. Lin et al., "Lifetime-based pH sensors: indicators for acidic environments", Analytical Biochemistry 1999, 269, 162-167). In this context, however, a difference has to be drawn between a sensor dye in solution and a sensor dye immobilized in a polymer matrix. With the immobilizing of a sensor dye in a polymer matrix, interactions can occur which change the optical properties of the sensor dye.

In the manufacture of pH optodes, pH-sensitive dyes are normally immobilized in water-permeable polymers. With combinations of polymer matrix and sensor dye used up to now, changes on the optical properties of pH-sensitive dyes have occurred which severely restrict the usefulness of the corresponding optodes. These changes in the optical properties result in these state-of-the-art optodes losing the property of change in the fluorescence decay time of the pH-sensitive dye as a function of pH value. A direct measurement of pH via the decay time of a pH-sensitive dye is therefore impossible.

This is detrimental as, compared with the direct measurement of intensity, the measurement of the decay time has the important advantage that it is almost completely independent of the dye concentration within the sensor matrix and of fluctuations in intensity of the excitation source.

Loss of change in decay time as a function of pH value also then makes the use of special spectroscopic methods such as phase modulation spectroscopy impossible.

The dual state-of-the-art optodes for measuring pH and oxygen concentration also possess a pH measuring range from 5 to 7.5. The usefulness of these optodes is limited by this measuring range.

The purpose of this present invention is to eliminate the disadvantages of these state-of-the-art devices.

The purpose of the present invention is therefore to provide optodes with which the luminescence decay time of a pH-sensitive dye as a function of pH is retained—even after immobilizing the sensor dye in a polymer matrix. The purpose of the present invention is also to provide optodes which, in addition to determining the pH, allow the determination of further chemical parameters, especially as a simultaneous measurement. In this, the optode for spatially resolved, real-time measurement shall be used.

The purpose of the present invention is also to provide an optode for the simultaneous determination of the pH and oxygen concentration which enables pH measurements below the value of 5.

The purpose of the present invention is satisfied by the features of the independent claims 1 and 15. Advantageous statements are given in the sub-claims.

The purpose of the invention is satisfied by the provision of an optode for determining chemical parameters of a sample wherein the optode consists of a polymer matrix which consists of sulfonated polyether ether ketone (SPEEK) in which a sensor dye is immobilized or more than one sensor dye is immobilized, wherein at least one of the immobilized sensor dyes is pH-sensitive.

Especially advantageous is an optode with which in the sulfonated polyether ether ketone (SPEEK) at least one further sensor dye is immobilized. Preferred is also an invention-related optode that consists of at least one further polymer matrix, in which at least one further sensor dye is immobilized Invention-related preference is that, with the invention-related optode at least one further sensor dye is selected from oxygen-sensitive, halide ion-sensitive, sodium ion-sensitive, potassium ion-sensitive, pH-sensitive and calcium ion-sensitive dyes.

Preferred is an optode with which the pH-sensitive sensor dye selected is from 4-{4-[4-(dipentylamino)phenyl]-1,3-butadienyl}-1-(4-sulfobutyl)pyridinium hydroxide (RH421, bis-(1,3-dibutylbarbituric acid)trimethineoxonol (Di-bac$_4$(3)), 6-carboxyfluorescein (CF), 5(6)-carboxy-2',7'-dichlorofluorescein (Cl-CF) and 8-hydroxy-1,3,6-pyrenetrisulfonic acid-trisodium salt (HPTS).

Especially advantageous is an optode with which the oxygen sensitive dye selected is from Pt(II)meso-tetra(pentafluorophenyl)porphyrin (Pt-TPFPP), Pd(II)meso-tetra(pentafluorophenyl)porphyrin and ruthenium(II)-tris(4,7-diphenyl-1,10-phenanthroline)perchlorate (Ru-pCl) and ruthenium(II)-tris(4,7-diphenyl-1,10-phenanthroline)dichloride;

the halide ion-sensitive dye selected is from the chloride ion-sensitive dyes N,N'-dimethyl-9,9'-bis-acridinium nitrate (Lucigenin), 6-methoxy-N-(3-sulfopropyl)quinolinium (SPQ) and N-(ethoxycarbonylmethyl)-6-methoxy-quinolinium bromide (MQAE);

the sodium ion-sensitive dye selected is from N,N'-[1,4,10-trioxa-7,13-diazacyclopentadecane-7,13-diylbis(2,5-dimethoxy-4,1-phenylene)]bis[3',6'-bis(acetyloxy)-2',7'-dichloro-3-oxo-spiro[isobenzofuran-1(3H),9'-[9H]xanthen]-5-carboxamide, (Sodium Green®, Molecular Probes, CAS Registry-Number 159952-49-5) and N-(4-[1-(7-diethylaminocoumarin-3-yl)-1H-1,2,3-triazol-4yl]phenylaza-18-crown-6-ether;

the potassium-sensitive dye is N-(2-methoxyethoxy)phenylaza-18-crown-6)-4-(coumarinyl)-1H-1,2,3-triazol
and
the calcium ion-sensitive dye is selected from the calcium ion-sensitive dye N-[2-[(acetyloxy)methoxy]-2-oxoethyl]-N-[4-[[[3',6'-bis(acetyloxy)-2',7'-difluoro-3-oxospiro[isobenzofuran-1(3H),9'-[9H]xanthen]-5-yl]carbonyl]amino]-2-[2-[2-[bis[2-[(acetyloxy)methoxy]-2-oxoethyl]amino]phenoxy]ethoxy]phenyl]-glycine-(acetyloxy)methyl ester (Oregon Green™ 488 BAPTA-1), N-[2-[2-[2-[bis(carboxymethyl)amino]-5-[[(2',7'-difluoro-3',6'-dihydroxy-3-oxospiro[isobenzofuran-1 (3H),9'-[9H]xanthen]-5-yl)carbonyl]amino]phenoxy]ethoxy]-6-fluorophenyl]-N-

(carboxymethyl)-glycine-hexapotassium salt (Oregon Green™ 488 BAPTA-6F) and N-[2-[2-[2-[bis(carboxymethyl)amino]-5-[[(2',7'-difluoro-3',6'-dihydroxy-3-oxospiro[isobenzofuran-1(3H),9'-[9H]xanthen]-5-yl)carbonyl]amino]phenoxy]ethoxy]-5-nitrophenyl]-N-(carboxymethyl)-glycine-hexapotassium salt (Oregon Green™ 488 BAPTA-5N).

Also preferred is an optode, with which the polymer of at least one further polymer matrix is selected from poly(2,2,2-trifluoroethylmethacrylate) (P1), poly(2-hydroxypropylmethacrylate) (PHPMA), poly(2-hydroxyethylmethacrylate) (PHEMA), polyurethane (PU), polyvinylpyrrolidone (PVP), poly(1-vinylpyrrolidone)-co-styrene (PVPS), polyvinylchloride (PVC), polyacrylonitrile-polyacrylamide-blockcopolymer (HYPAN HN 80) and polystyrene.

Invention-related special preference is an optode with which the pH-sensitive dye is 6-carboxyfluorescein (CF) or 5(6)-Carboxy-2,7'-dichlorofluorescein (Cl-CF), the further polymer is a poly(2,2,2-trifluoroethylmethacrylate)matrix and the oxygen-sensitive dye is Pt(II)meso-tetra(pentafluorophenyl)porphyrin or Pd(II)meso-Tetra(pentafluorophenyl)porphyrin.

Advantageous is an optode which consists of two further polymer matrices, wherein the first further matrix includes the polymer poly(2-hydroxypropylmethacrylate), in which the chloride ion-sensitive dye N,N'-dimethyl-9,9'-bisacridiniumnitrate is immobilized, and the second further polymer matrix includes the polymer poly(2,2,2-trifluoroethylmethacrylate), in which the oxygen-sensitive dye Pt(II)meso-tetra(pentafluorophenyl)porphyrin (Pt-TPFPP) oder Pd(II)meso-Tetra(pentafluorophenyl)porphyrin (Pd-TPFPP) is immobilized.

Preferred is also an invention-related optode whose polymer layer, in which the sensor dye is immobilized or between the polymer layers in which one or more sensor dyes are immobilized, a further layer or several further layers are applied, wherein no sensor dye is immobilized in this at least one further separation layer.

Preferred is also an invention-related optode, which includes at least one substrate on which the one or the several polymer matrices and the sensor dyes immobilized there are fixed.

Especially advantageous is an optode with which the at least one substrate is selected from glass substrates or polymer substrates.

Especially advantageous is an optode in which the substrate is formed from a polymer matrix in which a sensor dye is immobilized.

Advantageous in invention terms is an implementation form which is connected to one or more fiber optic conductors or part of a fiber optic conductor.

The purpose of the present invention is also satisfied by a method for determining the pH of a sample in which the invention-related optode is used.

Especially preferred is a method with which, in addition, carbon dioxide concentration and/or ammonia concentration and/or oxygen concentration and/or halide ion concentration and/or sodium ion concentration and/or potassium ion concentration and/or calcium ion concentration of the sample can be determined and the determination of the parameters can be performed simultaneously or time-shifted.

Especially preferred is a method with which the determination of the parameter or parameters is performed as stationary or time-resolved and the determination of the parameter or parameters using microscope, CCD camera reflection spectroscopy, fluorescence spectroscopy, time-domain spectroscopy and/or phase-modulation spectroscopy.

Surprisingly, it was found that use of the sulfonated polyether ether ketone (SPEEK) for immobilizing a pH-sensitive dye allows the optical determination of the pH via the luminescence decay time of the sensor dye. Unlike other previously investigated matrices, the change in the decay time of the pH-sensitive dye is retained after the immobilization in SPEEK. This means that performing of time-resolved optical methods to determine the pH is possible in real time.

The immobilizing of a further sensor dye in the SPEEK matrix of the invention-related optode enables the determination of further chemical parameters and also the determination of pH in different pH ranges by combining various pH-sensitive dyes. This therefore reduces the technical effort required when compared with the use of several individual optodes.

The immobilization of a further sensor dye in a further polymer matrix has the advantage that further parameters of the sample, in addition to the pH, can be determined using one optode. In addition, the further polymer matrix can be individually adapted to the other parameters to be measured and to the immobilized sensor dye. For example, the determination of a gas concentration requires a polymer matrix that is permeable to gas. It can also be an advantage, depending on the sensor dye, to use a polymer material that has an adapted polarity.

It is also an advantage with the invention-related optode that a large number of parameters can be determined, in addition to pH, so reducing the technical effort required, compared with individual measurement of the parameters. Especially when examining biological samples, the potential for miniaturization in optical appliances is an advantage, which is supported even further when just one optode can be used for the simultaneous determination of several parameters.

The possibility of immobilizing different pH-sensitive sensor dyes in the invention-related optode enables measurement in different pH ranges while retaining the invention-related benefits. By immobilizing various further sensor dyes, the invention-related optode can be adapted in its sensitivity and measuring range to different substance concentrations.

The large number of polymers that can be used as a further polymer matrix makes possible the adaptation of the invention-related optode to the parameters to be measured and the sensor dyes used. This makes possible an individual tuning of the optode to the area of application.

The optode can be combined with a suitable carrier, depending on the range of the application. Carriers can be made from a wide variety of materials, for example glass or polymers.

If glass carriers are used, these can for example be a planar glass body such as a slide and the optode material can be deposited as a film on the carrier.

In certain applications, it can be of benefit to separate the sensor dye bearing polymer matrices from each other using one or more material layers (separating layers) or to isolate from certain media. These separating layers do not contain sensor dyes. For example, such separating layers can be of advantage in the measurement of carbon dioxide and ammonia concentrations using the invention-related optode. In this, a material layer that is gas-permeable but water-impermeable can be applied on the SPEEK/pH-sensor dye object. The determination of carbon dioxide and ammonia concentrations can then take place by measuring the pH, without falsification of the result from non-gaseous media, e.g. liquids in the surroundings.

If a light conductor such as an optical fiber is used as a carrier, the optode material can be arranged for example on the tip of a fiber of the light conductor. It is however also preferred that the optode material is arranged on several fibers of a conductor so that measurements are possible at different positions in a sample.

If the invention-related optode consists of more than one polymer material in which a sensor dye is immobilized, the polymer/dye layers can be deposited in any order on the carrier.

The invention-related optode for determining several parameters can also be applied to the carrier in such a way that the optode material is not applied in successive layers on a carrier but only in spatial proximity to each other. Spatial proximity here means that the arrangement enables a simultaneous measurement of both parameters.

In one implementation form of the present invention, SPEEK containing the immobilized sensor dye is applied to the fiber and the further polymer matrix is arranged on the fiber next to this optode material. Overlapping of the layers can occur here or the attachment of the further polymer matrix can take place without overlapping.

In a further implementation form, it is preferred to coat the ends of a glass fiber with the optode material components so that, for example, one fiber carries the SPEEK matrix for determining pH and one or more further fibers the polymer matrices for determining the further parameter or parameters.

Also preferred is the use of polymer materials as carriers for the optode material. Here, the optode material can be applied to a polymer carrier, for example in the form of a polymer particle such as polymer beads.

Preferred is also that an optode material component, i.e. a polymer matrix with immobilized sensor dye serves itself as carrier for further polymer/sensor dye combinations. This is especially advantageous when fiber optic systems are unsuitable for the corresponding applications, for example the systems to be investigated are closed and insertion of the fiber sensor is not possible. In this case, the optode can be inserted directly into the sample in the form of a polymer particle. The process to be investigated can be followed from outside by optical interrogation of the bead-shaped probe. The optical signal can be detected here by means of a microscope or optical fibers.

Preferred implementation examples of the present invention are explained in the following text. In this context, general and special methods are described. In the following text, the term "optode material" is understood in the context of the present invention as the polymer matrix/sensor dye combinations of the invention-related optode.

Sensor Dyes Used, Polymers and Additives

The following sensor dyes, polymers and additives were used in the implementations described below. The other polymers and sensor dyes are commercially available.

The abbreviations used, the sources and (if applicable) degree of purity are shown in brackets. The Chemical Abstracts Services registry number is listed if it is known.

Polymers and Additives

Sulfonated Poly(Ether Ether Ketone) (SPEEK)

The sulfonated poly ether ether ketone (SPEEK) was prepared in the Fraunhofer Institute for Interfacial Engineering and Biotechnology IGB, Stuttgart, Germany. On this, see K. S. Roelofs et al. "Behavior of sulfonated poly(ether ether ketone) in ethanol-water systems", J. of Applied Polymer Science 2009, 111, 2998-3009, K. S. Roelofs et al., "Sulfonated poly(ether ether ketone)-based silica nanocomposite membranes for direct ethanol fuel cells", J. of Membrane Science 2010, 346, 215-226.

The preparation of the sulfonated polyether ether ketone used can be taken from Huang et al., "Sulfonation of Poly(Ether Ether Ketone) (PEEK): Kinetic Study and Characterization", J. Applied Polymer Science, 2001, Vol. 82, 2651-2660.

In this, polyether ether ketone (PEEK) is dissolved in concentrated sulfuric acid. The sulfonation takes place during a rise in temperature over a period of several hours. The degree of sulfonation (DS) is set by the choice of reaction temperature and reaction time. The degree of sulfonation is the ratio of concentration of sulfonated PEEK repeat units (see Formula 1) to the concentration of the entire initial PEEK repeat units. For the purposes of the present invention, SPEEK with a 40 to 80% degree of sulfonation was used.

Formula I

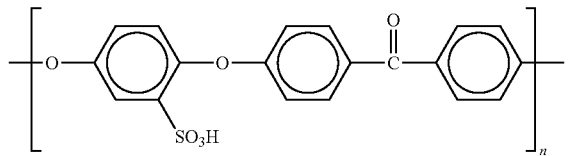

Repeat unit of the sulfonated polyether ether ketone

Formula 2 shows SPEEK with a degree of sulfonation under 100%.

Formula 2

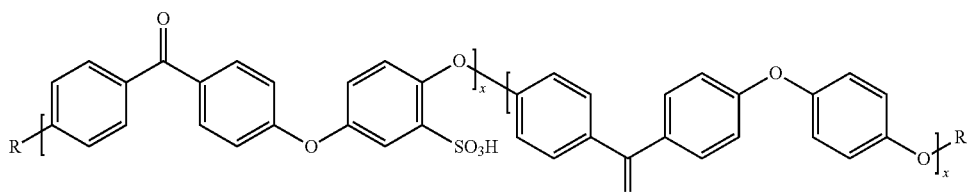

SPEEK

Polymers and Additives 1,4-diazabicyclo(2.2.2)octane (98%, DABCO, Aldrich, CAS Registry No. 280-57-9);

Ormosil: Ormosil was synthesized according to I. Klimant et al., "Fast response oxygen micro-optodes based on novel soluble ormosil glasses", Mikrochim. Acta 1999, 131, 35-46;

HYPAN HN 80; hydrogel, (CAS Registry No. 167290-73-5) block copolymer from polyacrylonitrile and polyacrylamide;

Poly(2,2,2-trifluoroethylmethacrylate), (P1, Aldrich, CAS Registry No. 54802-79-8);

Poly(2-hydroxypropylmethacrylate) (PHPMA, Aldrich, CAS Registry No. 25703-79-1);

$SiO_2$ (Aerosil R972, Degussa, CAS Registry No. 60842-32-2)

Sensor Dyes

Platinum(II)meso-tetra(pentafluorophenyl)porphyrin (Pt-TPFPP, Frontier Scientific, Inc, CAS Registry-No. 109781-47-7);

Palladium(II)meso-tetra(pentafluorophenyl)porphyrin (Pd-TPFPP, Frontier Scientific, Inc, CAS Registry No. 72076-09-6);

Ruthenium(II)-tris(4,7-diphenyl-1,10-phenanthroline) perchlorate (Ru-pCl, H. W. Sands, Corp.; CAS Registry No. 75213-31-9)

Ruthenium(II)-tris(4,7-diphenyl-1,10-phenanthroline)dichloride (Aldrich, CAS Registry No. 36309-88-3);

6-Carboxyfluorescein/IUPAC-Name: 3',6'-dihydroxy-1-oxospiro[2-benzofuran-3,9'-xanthen]-5-carboxylic acid (98%, CF, Aldrich, CAS Registry-No. 3301-79-9);

5(6)-carboxy-2',7'-dichlorofluorescein (98%) (Cl-CF, Aldrich, CAS Registry-No. 111843-78-8);

8-hydroxy-1,3,6-pyrenetrisulfonic acid-trisodium salt (HPTS, CAS Registry-No. 27928-00-3);

4-{4-[4-(dipentylamino)phenyl]-1,3-butadienyl}-1-(4-sulfobutyl)pyridinium hydroxide (RH421; Aldrich, CAS Registry-No. 107610-19-5)

Bis-(1,3-dibutylbarbituric acid)trimethine oxonol ($Dibac_4$(3), Aldrich, CAS Registry-No. 70363-83-6)

2',7'-bis-(2-carboxyethyl)-5(6)carboxyfluorescein (BCECF, Aldrich, CAS Registry-No. 85138-49-4);

N,N'-dimethyl-9,9'-biacridiniumdinitrate (Lucigenin, Aldrich, CAS Registry-No. 2315-97-1);

6-methoxy-N-(3-sulfopropyl)quinolinium (SPQ, CAS Registry-No. 83907-40-8);

N-(ethoxycarbonylmethyl)-6-methoxyquinolinium bromide (MQAE, Aldrich, CAS Registry-No. 162558-52-3);

N,N'-[1,4,10-trioxa-7,13-diazacyclopentadecane-7,13-diylbis(2,5-dimethoxy-4,1-phenylene)]bis[3',6'-bis(acetyloxy)-2',7'-dichloro-3-oxo-spiro[isobenzofuran-1(3H),9'-[9H]xanthen]-5-carboxamide, (Sodium Green®, Molecular Probes, CAS Registry-No. 159952-49-5);

N-(4-[1-(7-diethylaminocoumarin-3-yl)-1H-1,2,3-triazole-4yl]phenylaza-18-crown-6-ether (see Sandra Ast et al., Chem. Commun., 2011, 47, 4685-4687);

N-(2-[1-(-4-diethylaminocoumarin-3-yl)-1H-1,2,3-triazole-4yl]phenylaza-18-crown-6-ether (see Sandra Ast et al., Chem. Commun., 2011, 47, 4685-4687);

N-[2-[(acetyloxy)methoxy]-2-oxoethyl]-N-[4-[[[3',6'-bis(acetyloxy)-2',7'-difluoro-3-oxospiro[isobenzofuran-1(3H),9'-[9H]xanthen]-5-yl]carbonyl]amino]-2-[2-[2-[bis[2-[(acetyloxy)methoxy]-2-oxoethyl]amino]phenoxy]ethoxy]phenyl]-glycine-(acetyloxy)methyl ester (Oregon Green™ 488 BAPTA-1), N-[2-[2-[2-[bis(carboxymethyl)amino]-5-[[(2',7'-difluoro-3',6'-dihydroxy-3-oxospiro[isobenzofuran-1(3H),9'-[9H]-xanthen]-5-yl)carbonyl]amino]phenoxy]ethoxy]-6-fluorophenyl]-N-(carboxymethyl)-glycine-hexapotassium salt (Oregon Green™ 488 BAPTA-6F) and N-[2-[2-[2-[bis(carboxymethyl)amino]-5-[[(2',7'-difluoro-3',6'-dihydroxy-3-oxospiro[isobenzofuran-1(3H),9'-[9H-1]xanthen]-5-yl)carbonyl]amino]phenoxy]ethoxy]-5-nitrophenyl]-N-(carboxymethyl)-glycine-hexapotassium salt (Oregon Green™ 488 BAPTA-5N).

See, for example, Yoshiki et al., Optical Review Vol. 12, No. 5 (2005) 415-419 for the selection of other calcium-sensitive dyes.

ABBREVIATIONS AND SYMBOLS

The following abbreviations and symbols are used
FD-S: Frequency Domain Spectroscopy (phase modulation spectroscopy)
d-FD-S: FD-S using two modulation frequencies
TD-S: Time Domain Spectroscopy (pulse method)
LD: Laser diode
[X]: Concentration of X
$K_{SV}$: Stern-Volmer constant
E: Extinction
f: Modulation frequency
φ: Phase shift in degrees
λ: Wave length in nm
$\lambda_{em}$: Emission wave length
$\lambda_{ex}$: Excitation wave length
Int (λ=X nm): Fluorescence intensity at $\lambda_{em}$=X nm
τ: Luminescence decay time
(τ): average decay time from TD-S measurements
$\tau_0$: Decay time when an analyze is not present (extinguisher)
$\tau_S$: apparent decay time (FD-S)
U: Detector voltage (α luminescence intensity)
V: Volume

BRIEF DESCRIPTION OF THE FIGURES

FIG. 2 B shows the average decay time, calculated from the results of biexponential fits FIG. 3 A shows the decay curves of Cl-CF, immobilized in SPEEK as a function of pH, at constant NaCl concentration: 0.3 mol/L ($\lambda_{ex}$=460 nm; $\lambda_{em}$=520 nm)

FIG. 5 B shows the intensity ratio when evaluating at various emission wavelengths;

FIG. 6 B shows the intensity ratio (quotient) when evaluating at various emission wavelengths;

FIG. 7 B shows the evaluation of the intensity at various emission wavelengths.

FIG. 11 B shows the response characteristics when changing from pH=2 to pH=6;

FIG. 12 B shows the decay times of Pt-TPFPP immobilized in P1 as a function of pH ($\lambda_{ex}$=405 nm; $\lambda_{em}$>600 nm);

FIG. 13 A shows the measurement at 21 vol % oxygen, FIG. 13 B shows the measurement at 0 vol % oxygen;

FIG. 14 A shows the measurement at pH=4, FIG. 14 B shows the measurement at pH=1.3;

FIG. 15 A shows the pH signal at various wavelengths and $O_2$ concentrations, FIG. 15 B shows the Stern-Volmer graph of intensities at 650 nm for various pH values.

FIG. 16 A shows decay times and intensities of CF in SPEEK in oxygen-free and air-saturated buffer solutions ($\lambda_{ex}$=405 nm; $\lambda_{em}$=505 nm-580 nm); FIG. 16 B shows decay times of Pt-TPFPP immobilized in P1 as a function of pH and oxygen concentration ($\lambda_{ex}$=405 nm; $\lambda_{em}$>600 nm). Both optode materials are located on a fiber.

FIG. 17 B shows the Stern-Volmer plot of the $O_2$ signal.

FIG. 19 A shows the result using triexponential fit to the decay curves;

FIG. 19 B shows the Stern-Volmer graph using the mean decay time ($\tau$).

PRODUCTION OF INVENTION-RELATED OPTODE AND OPTODES FOR CALIBRATION

Production of Invention-Related Optodes

Figure 1:
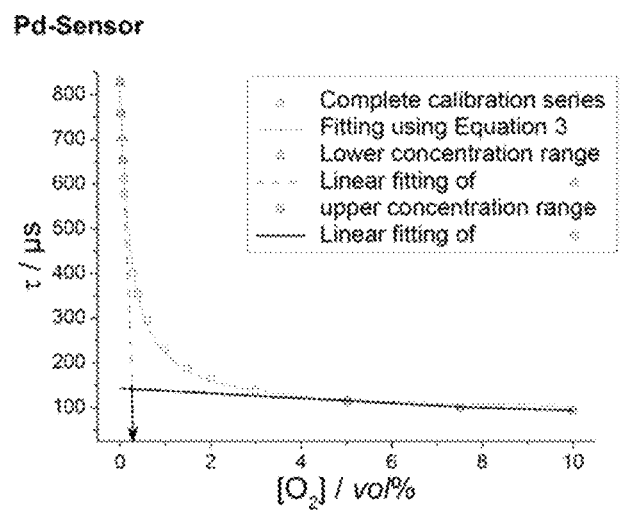
FIG. 1 shows the calibration of an optode for determination of oxygen concentration in the example of the oxygen-sensitive Pd sensor (palladium(II)-meso-tetra(pentafluorophenyl)porphyrin, immobilized in poly(2,2,2-trifluoroethylmethacrylate) (P1)), and a ruthenium-based sensor (ruthenium(II)-tris(4,7-diphenyl-1,10-phenanthroline)-perchlorate immobilized in polystyrene beads)
Figure 1:
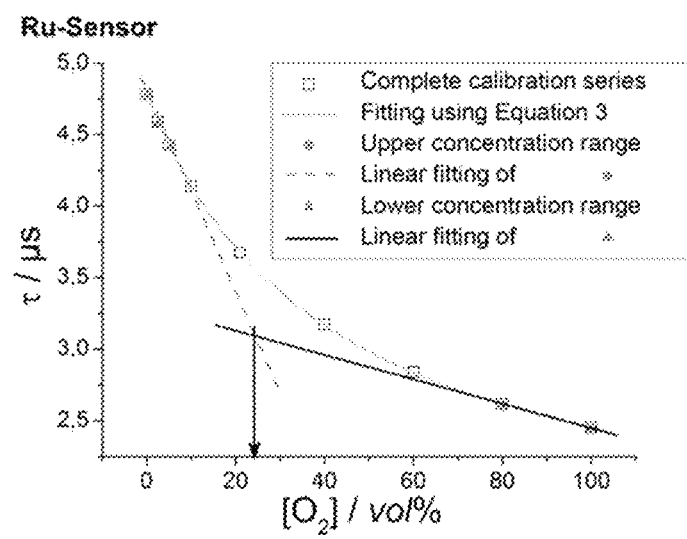

In the production of invention-related optodes, at least one pH-sensitive dye is immobilized in SPEEK polymer. To determine other parameters using the optode, further sensor dyes must be integrated into the SPEEK membrane. It is also preferred that the invention-related optode includes further polymer matrices, in which sensor dyes are immobilized.

When selecting other suitable sensor dyes, for example oxygen-sensitive dyes, it is recommended that the emission wavelengths of the sensor dyes differ from each other. The sensor dyes are so selected that they can be separated spectrally. In preferred implementation examples, the emission wavelength of further sensor dyes was greater than 600 nm.

Immobilizing of Sensor Dyes in SPEEK

To immobilize the sensor dyes in the polymer matrices, SPEEK is swollen in an aqueous solution with a solution of the appropriate sensor dye.

Immobilizing of Sensor Dyes in Other Polymer Matrices

In an implementation example of the present invention, the polymers are swollen using an aqueous solution of the particular sensor dye (pH≈6.5–7, concentration: $1.0 \times 10^{-4}$ mol/L).

Depending on the polarity of the polymer, the immobilization of the sensor dye can for example also occur due to the swelling of the polymer in ethanol and the addition of an alcohol-based solution of the corresponding dye. Once the components have been combined, the mixture is homogenized, by shaking for example.

Production of the Invention-Related SPEEK/CF and SPEEK-Cl-CF Optodes 0.3 g dry SPEEK (DS=60%) is swelled in a mixture of 4 mL distilled water and 100 µL dye solution (CF or Cl-CF, c=0.002 mol/L). During the swelling process, the mixture is shaken in a mechanical shaker (800 rμm). The solution loses its color within 3 hours as the polymer absorbs the dye. The SPEEK/dye mixture is then removed and put in water (distilled, adjusted to pH=7 using dilute NaOH) and left for at least 8 hours at a temperature of 60-65° C. The cooled SPEEK/dye mixture is then pressed between two microscope slides, which are weighted down with 2-kilogram metal blocks. This produces thin layers after a period of at least 10 hours. The material is then left to dry at 80° C. in a drying cabinet (at least 6 hours). Using a scalpel, small (1/×1×1) mm pieces are cut to size (then halved for the dual optode). One piece is then attached to a polished fiber surface using UV adhesive (Norland NOA 63).

Production of Lucigenin/PHPMA Optode 0.3 g of dry PHPMA is added to a 0.005 molar aqueous Lucigenin solution (pH between 5-6). The polymer begins to swell and absorbs the dye. The mixture is shaken at 800 rμm for 3 hours. Using a scalpel, small (1×1×1) mm pieces are cut to size, the thickness of the pieces should be less than 0.5 mm, otherwise the response time of the optode material is too long. After being dried at 65° C., the polymer is attached to the polished tip of a fiber—as described above for SPEEK/CF and SPEEK/Cl-CF optodes.

Production of Pt-TPFPP/P1 and Pd-TPFPP/P1 Optode Materials 2.8 mg Pt-TPFPP or 2.6 mg Pd-TPFPP were dissolved in 2 ml butanone. 154 mg poly(2,2,2-trifluoroethylmethacrylate) (P1), 3.71 mg DABCO, 1 mg $SiO_2$ (Aerosil® R972) and 39 mg Ormosil are added to these solutions. A fiber to be coated is dipped into the resulting, slightly viscous solution. A microscope (Zeiss Axiostar) is used to check whether the tip is completely and uniformly coated. The optical fiber is laid in a drying cabinet at 65° C. to dry out. A 1 mm-thick fiber was used.

Production of the Invention-Related CF/SPEEK-(Pt-TP-FPP)/P1 Optode

The Pt-TPFPP dye was first immobilized, as described above, in polymer P1, a 1 mm-thick fiber dipped into the polymer/sensor dye mixture and dried as described above.

With a paper towel soaked in isopropanol, the coating in a part area of the fiber surface, half of the coated area in the present case, is completely removed so that there are no dye residues remaining on this part of the fiber. A thin layer of UV adhesive is now applied to the cleaned half of the fiber area and piece of SPEEK placed there using tweezers. Fluorescence microscopy is used to check that the layers do not overlap.

Attaching to a Carrier/Carrier Materials

The attaching of the optode material to a carrier can be done using any method that is recognized as state-of-the-art.

For fiber-based investigations in which the carrier is an optical fiber, the optode material can be made by dipping a fiber end into the polymer in which the sensor dye is immobilized. For fixing, drying in a heating device may be required. A suitable adhesive can also be used for fixing.

It can also be sufficient in certain investigations to prepare the optode material on a glass slide. The optode material, the SPEEK and dye immobilized in these can only be dissolved in low-volatility solvents. For the production of thin layers, the swollen optode material can be pressed between two glass slides. Layers of different thickness can be produced in this way. Layers with a thickness of between 300 μm and 500 μm are produced in this way for optical investigations.

In the context of the present invention, optical fiber conductors, among others, were used as carrier material. The selection of suitable material is known to experts.

All optical MM (multi-mode) glass fibers used in the context of the invention were coated with a special non-fluorescing silicone coating manufactured by the FiberTech company.

For oxygen analysis, fibers with a core diameter of 100 μm were used. For the intensity-based pH measurements, four 100 μm fibers were combined into a bundle; one fiber was used as the detection fiber, the other three fibers were used to carry the excitation light to the optode. In decay time measurements for the pH determination, fibers with a core diameter of 1 mm were used. The excitation was done via a 430 μm fiber, which was simultaneously glued to the detection fiber (also with a core diameter of 430 μm) in an SMA connector and with the 1 mm fiber to which the optode was attached.

In the case of optodes which determine two parameters (dual-optodes), three fibers with a diameter of 430 μm were glued into an SMA connector with a hole diameter of 1000 μm (Schwanheimer Industrie instant adhesive). The connector was smoothed off using diamond abrasive paper and then polished. Both optode materials were then attached to a 1 mm fiber and coupled by means of the SMA connector to the plug of the three fibers. One of the three fibers is used for the excitation and the other two for detection of pH and $O_2$-dependent emissions.

Production of the Invention-Related CF/SPEEK-(Pt-TP-FPP)/P1-Lucigenin/PHPMA Optode The following materials were applied in succession to the tip of the fiber: Pt-TPFPP, immobilized poly(2,2,2-trifluoroethylmethacrylate) (P1), Lucigen, immobilized in poly(2-hydroxypropylmethacrylate) (PHPMA) and 6-carboxyfluorescein, immobilized in SPEEK.

Preliminary Trials and Calibrations

Calibration of the Optodes

Before the optodes can be used for the analysis of unknown samples, they must be calibrated in defined solutions. This must therefore be done for each sensor individually as the coatings on the optode tips can differ from each other.

Calibration of the pH Optodes

Buffer solutions are used for the calibration of the optodes as the stability of the pH value is higher here despite changes in the composition. These consist of weak acids and their salts, as well as a strong base. Buffer solutions in the range 7.2 to 9 are made from mixtures of tris(hydroxymethyl)-aminomethane solution and hydrochloric acid. For the range pH 1 to 6.5, mixtures of citric acid monohydrate, sodium hydroxide and hydrochloric acid are manufactured. The composition used was that described by Rauscher et al. (Rauscher, Voigt, Wilke, Wilke, Chemische Tabellen and Rechentafeln für die analytische Praxis, volume 6, VEB Deutscher Verlag für Grundstoffindustrie, 1977, 140-145), and the pH checked with a standard glass electrode (WTW SenTix21). The pH meter for this was calibrated with standard buffer solutions (Carl Roth GmbH+Co. KG). For the checking of solutions with pH values between 0 and 8, standard buffers with pH=4.00±0.02 (citric acid/NaOH/NaCl) and pH=7.00±0.02 (phosphate mixture) were used; for the checking of solutions with pH>8, with standard buffers of pH=7.00±0.02 and pH=9.00±0.02 (boric acid/NaOH/KC).

The data of the calibrations were adjusted using the following sigmoidal function:

$$\tau = \frac{\tau_{A-} - \tau_{AH}}{1 + e^{\frac{pH - pK_S}{\Delta pH}}} + \tau_{AH} \qquad \text{(Equation 1)}$$

The difference $\tau_{A-} - \tau_{AH}$ describes the dynamics of the signal change of an optode, $\tau_{A-}$ represents the decay time of the deprotonated dye species, whereas $\tau_{AH}$ corresponds to the decay time of the protonated species. The inflection point of the calibration curve corresponds to the $pK_S$ value of the optode combination. Fluorescence intensities were also used instead of decay times.

Calibration of the Oxygen Optode

Because of the immobilization of the dye in a polymer matrix, different numbers of molecules are not accessible to the oxygen and so these always phosphoresce with the same decay time, depending on the condition of the optode. The Stern-Volmer graph shows no linear relationship, as not all dye molecules are equally accessible to the oxygen (quencher). This observation has often been made in connection with oxygen sensors (see, for example, Y.-L. Lo et al., "Temperature compensation of fluorescence intensity-based fiber-optic oxygen sensors using modified Stern-Volmer model", Sensors and Actuators B 2008, 131, 479-488.74, 106-109). The Stern-Volmer equation has to be extended for the data analysis:

$$\frac{\tau_Q}{\tau_0} = \frac{p}{1 + K_{SV} \cdot [Q]} + \frac{p_2}{1 + K_{SV,2} \cdot [Q]} \quad \text{dabei gilt: } p + p_2 = 1 \qquad \text{(Equation 2)}$$

In the solid state, the decay time and so also the Stern-Volmer constant of each immobilized dye molecule is dependent on its individual environment. In principle, the Stern-Volmer equation must be extended by any number of terms. The experimental data indicate however that it is sufficient when only two terms with $K_{SV,2}=0$ are used, which is why Equation 2 can be simplified to the modified Stern-Volmer equation (see E. Schmälzlin et al., "An optical multifrequency phase modulation method using microbeads for measuring intracellular oxygen concentrations in plants", Biophysical Journal 2005, 89, 1339-1345):

$$\frac{\tau_Q}{\tau_0} = \frac{p}{1 + K_{SV} \cdot [Q]} + (1-p) \quad \text{(Equation 3)}$$

The dye molecules are divided formally into two groups: those accessible to the quencher correspond to the fraction p, the remaining dye molecules are inaccessible to the oxygen. Here it concerns a parameter which depends on the layer thickness and the inhomogeneities of the optode material. The observed relationship between $\tau_0$ and the quencher concentration can be well described by Equation 3. The Stern-Volmer constant calculated using this equation cannot be compared with the constants of free dyes as the equation has been empirically derived.

Because of the non-linear nature of the modified Stern-Volmer equation, each sensor must be calibrated in practice at least three $O_2$ concentrations. Three suitable $O_2$ concentrations must be determined for each sensor dye, which depend on the dynamics of the dye. In this, the sensors were calibrated at more than ten different $O_2$ concentrations.

FIG. 1 shows, as an example, the calibration data of a Pd sensor (palladium(II)-meso-tetra(pentafluorophenyl)porphyrin, immobilized in poly(2,2,2-trifluoroethylmethacrylate) (P1), and a ruthenium-based sensor (ruthenium(II)-tris(4,7-diphenyl-1,10-phenanthroline)-perchlorate immobilized in polystyrene beads). The two sensor dyes show considerable differences in the dynamic range.

The decay time for the Pd sensor changes at concentrations between 0 and 10 vol % $O_2$. The ruthenium-based sensor also shows a significant change in decay time at very high $O_2$ concentrations. Equation 3 can be applied as calibration function for both sensors. The $O_2$ concentrations for the three-point calibration must however be adjusted to the respective dynamic range of the sensor. With both sensors, the $\tau_0$-value is defined by determining the decay time in the absence of oxygen. A further concentration is given by the maximum $O_2$ concentration at the upper limit of the dynamic range. The mean oxygen concentration should correspond to the value that results from the intersection of the two straight lines, which can be calculated from the first and last values of the calibration with as many concentrations as possible (FIG. 1). The use of these three $O_2$ concentrations can, with the help of the modified Stern-Volmer equation, ensure a valid calibration of the particular sensor over the entire dynamic range. When a different mean concentration is used, the calculated value for the parameter p and the Stern-Volmer constant deviate considerably from the values which result from the use of all ten measured concentrations. The calculation of the $O_2$ concentration would therefore lead, due to an imprecise calibration function, to false results.

The Stern-Volmer constants obtained with the use of various data points are shown in Table 1.

TABLE 1

| [O2] vol % | $K_{SV}$ (vol %)$^{-1}$ | p | $\tau_0$ μs |
|---|---|---|---|
| 0-10 (16 values) | 4.52 ± 0.08 | 0.8914 | 815.8 |
| 0; 10; 0.1 | 4.91 ± 0.31 | 0.8914 | 815.8 |
| 0; 10; 0.3 | 4.50 ± 0.27 | 0.8914 | 815.8 |
| 0; 10; 0.4 | 4.39 ± 0.28 | 0.8914 | 815.8 | p and $\tau_0$ were calculated from the 16-point calibration and regarded as fixed values in the following 3-point calibrations.

When using the oxygen concentration calculated via the intersection point, the $K_{SV}$ constant and therefore the calibration function are the best matches to the value which was calculated using all measured concentrations. This oxygen concentration of 0.3 vol % should also be used for calculation of the calibration function.

Furthermore, the value in the absence of oxygen ($\tau_0$) is determined for each sensor at the upper end of the dynamic range of the respective dye.

With the 3-point calibration for applications of the displayed Pd sensor, measurements should be made at 0 vol %, 10 vol % and 0.3 vol % oxygen. The decay times of the first two concentrations are noted in the measurement program. When measuring at 0.3 vol %, the p-value is varied so that the correct concentration is displayed. Care should be taken to determine the value of p as precisely as possible. A slight change in p (4%) leads to a significant change in the Stern-Volmer constant (40%) and so to a large deviation of the calibration function from the experimental data.

When determining oxygen concentrations by means of TD-S, no monoexponential decay curves are obtained. Because of the different environments of each dye molecule and the resulting different accessibilities for the quencher, the sensors show a distribution in the decay times. The calculation of the lifetime is made by means of the stretched exponential function (see Y. Cai et al., "Data analysis and aging in phosphorescent oxygen-based sensors", Sensors and Actuators B 2010, 146, 14-22.):

$$I(t) = I_0 \cdot e^{(-\frac{t}{\tau})\beta} \quad \text{(Equation 4)}$$

The parameter $\beta$ ($1 \geq \beta > 0$) gives the width of the distribution. The narrower the distribution, the closer $\beta$ is to the maximum value of 1. The smaller $\beta$ is, the wider is the decay time distribution.

Small values therefore indicate an inhomogeneity in the sensor matrix. The homogeneity of the optode material depends on the solubility of the dye and of analytes in the polymer.

pH Measurements pH value determinations were carried out on two implementation forms of the invention-related optodes. With the implemented examples, the pH sensor dyes: 6-carboxyfluorescein and 5(6)-carboxy-2',7'-dichlorofluorescein (Cl-CF) were immobilized in SPEEK.

A very slow (>30 min) initial response to pH changes was observed with the optode SPEEK/6-Carboxyfluorescein. To investigate the reaction to other ions, a series of measurements was performed with increasing NaCl concentration. A bi-exponential function was fitted to the decay curves. Especially at low NaCl concentrations, a component fluoresces with a short decay time of 1 ns; this component is no longer observed after the addition of NaCl. Up to an NaCL concentration of 0.6 mol/L, the mean decay time ($\tau$)

increases and then remains constant. Even after several washes and storage in deionized water, the decay time remains constant at over 2.5 ns. The process is therefore not reversible. If the optode material has been treated with NaCl solution, the response time is considerably shortened to under 5 minutes. With SPEEK, the addition of salt leads to an increase in the ability to absorb water, so the volume increases and the protons become more mobile.

Figure 2:
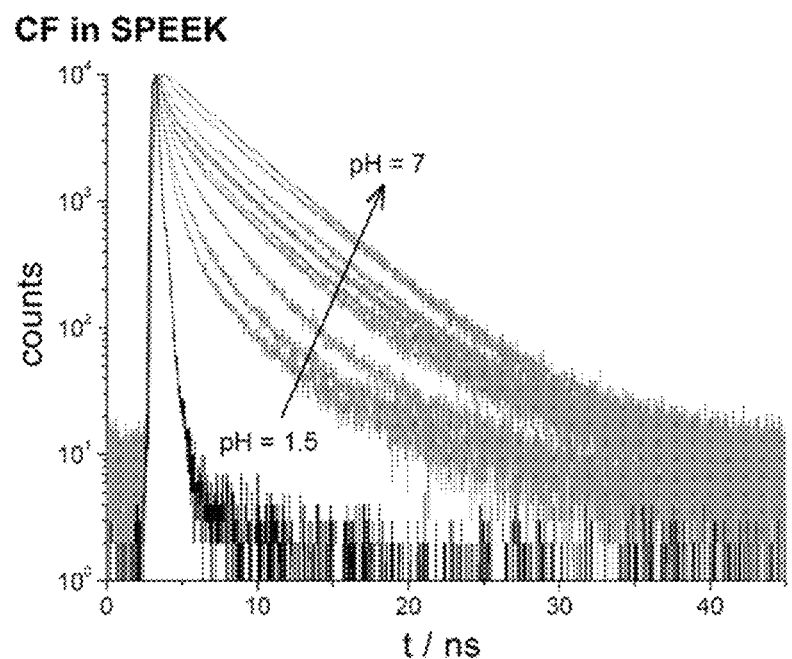
FIG. 2 A shows the decay curves of CF, immobilized in SPEEK, as a function of pH, constant NaCl concentration: 0.3, determination of the decay time of CF immobilized in SPEEK as a function of pH=0.3 mol/L.
Figure 2:
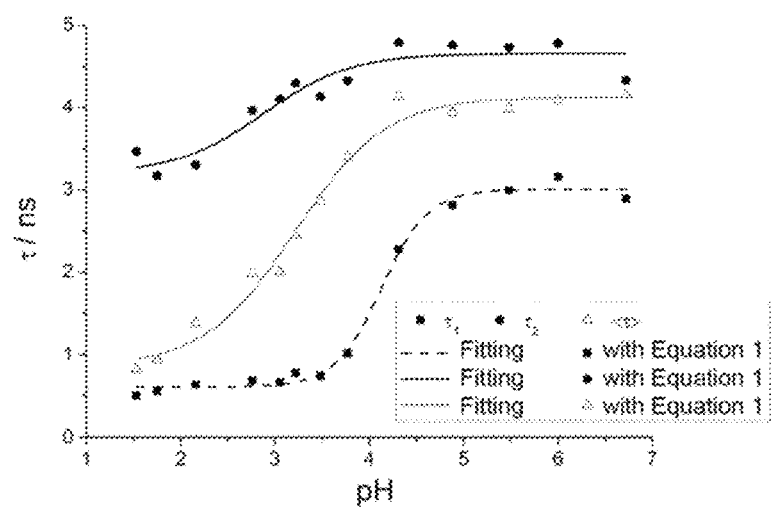

Determining decay time as a function of pH is shown in FIG. 2. The decay curves are evaluated using a bi-exponential function, wherein the decay times of the two components show different points of inflection, $\tau 1$ at pH=4.1 and $\tau 2$ at pH=2.9. The point of inflection of the calculated mean decay time ($\tau$) lies at pH=3.2.

Figure 3:
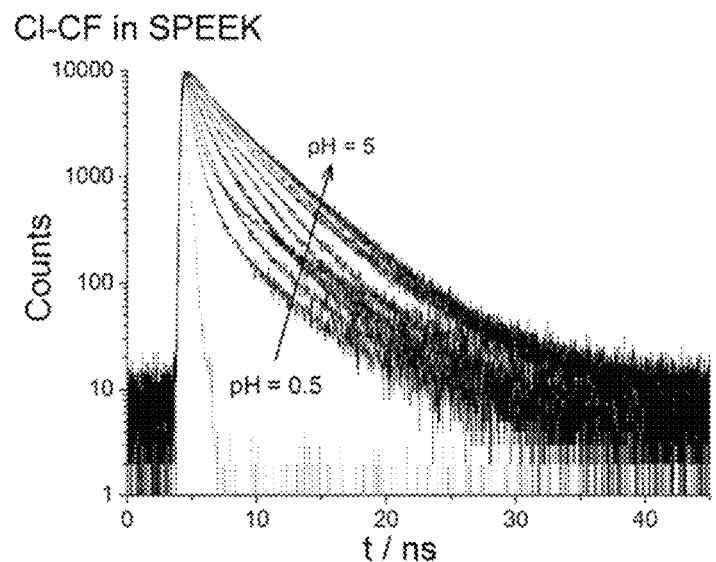
FIG. 3 B shows the average decay time, calculated from results of biexponential fits.
Figure 3:
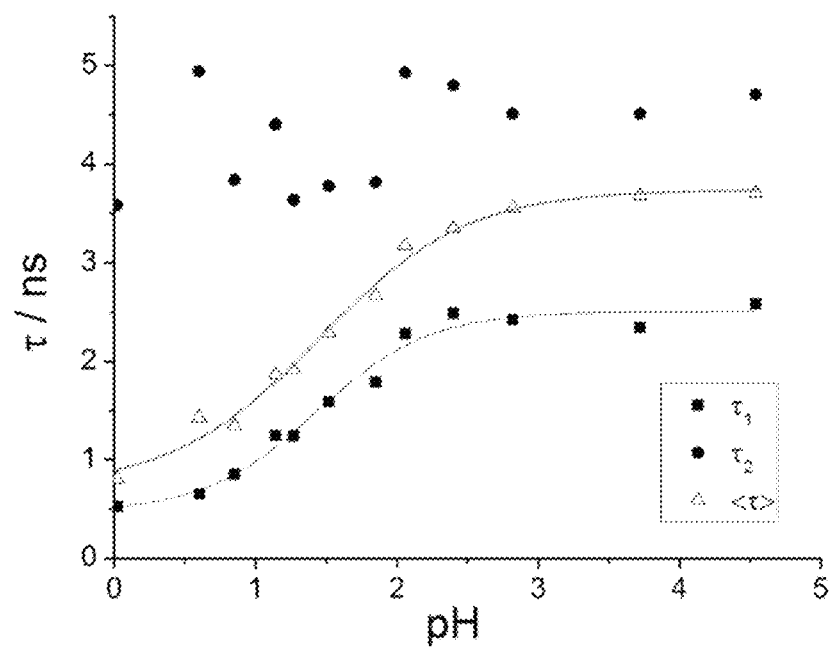

Corresponding measurements were performed with 5(6)-carboxy-2',7'-dichlorofluorescein (Cl-CF) (FIG. 3). The decay time here fluctuates between 3.5 ns and 5 ns while the other increases with pH. The point of inflection lies at pH=1.4.

It was found that in the SPEEK immobilized pH-sensitive dyes CF and Cl-CF, the decay time remains dependent on pH value. The points of inflection however do not match those determined for the sensor dyes in solution.

Figure 4:
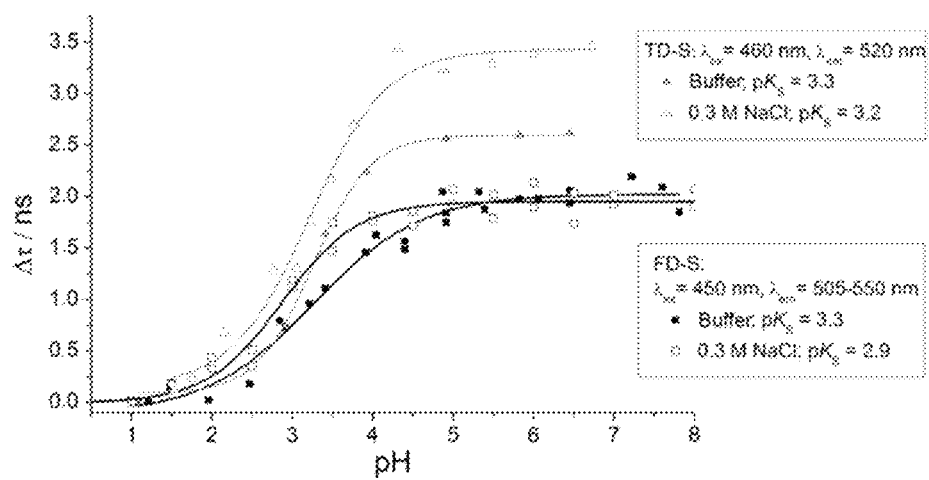
FIG. 4 shows the decay times of CF immobilized in SPEEK as a function of pH and background electrolyte, measured using FD-S (f1=30 MHz) at the microscope workplace.

Before characterizing the optode material using fiber sensors, phase modulation spectroscopy measurements (FD-S measurements) were performed at a microscope workplace (FIG. 4). The calibrations of time-domain spectroscopy (TD-S) measurements are added to the figure for comparison.

As already determined in solution by the inventors, the decay times at higher pH values determined using TD-S are about one nanosecond longer than those determined using FD-S. The points of inflection lie however in the same range and are shifted by a higher salt content in the direction of smaller pH values.

Intensity-Based Fluorescence of the Invention-Related SPEEK/CF Optode

Figure 5:
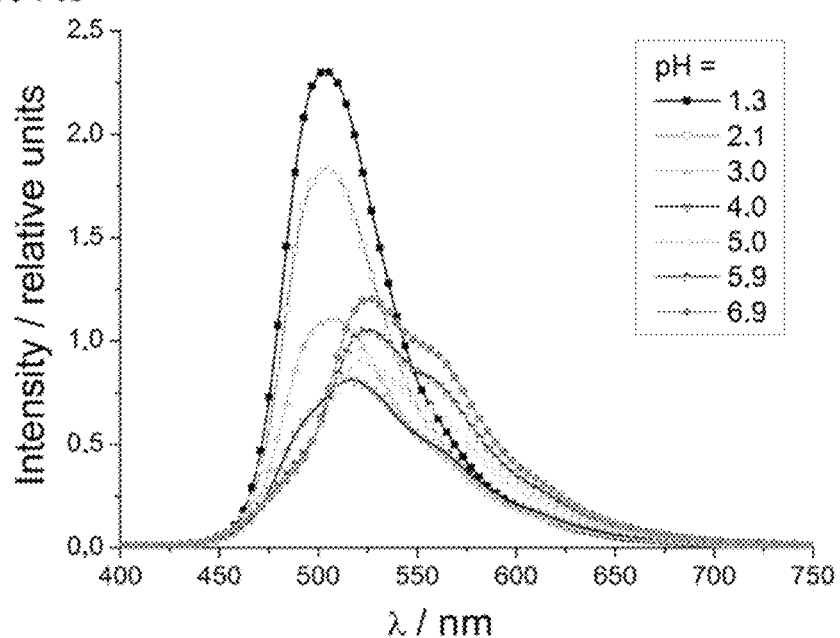
FIG. 5 A shows fluorescence spectra of immobilized CF ($\lambda_{ex}$=440 nm) in SPEEK at various pH values.
Figure 5:
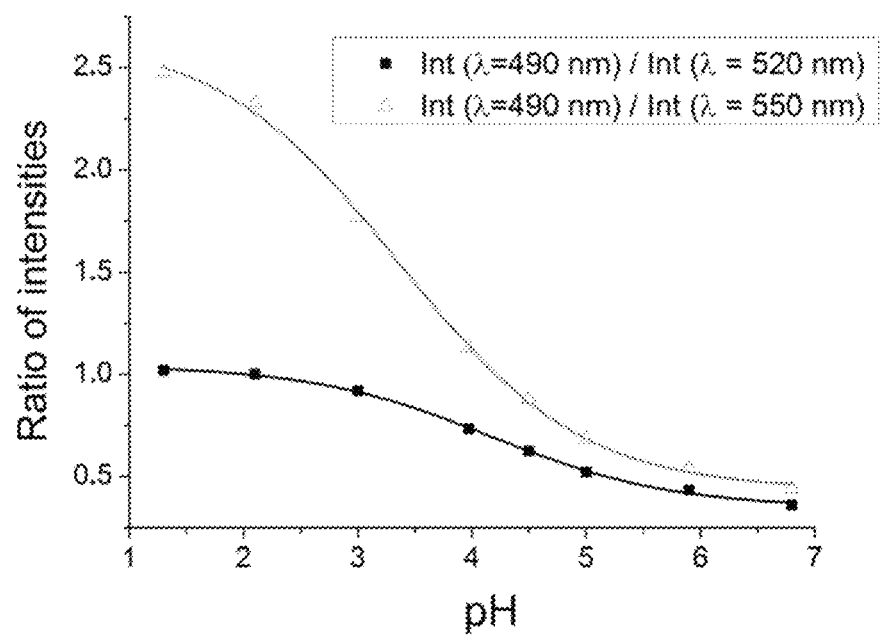

FIG. 5 shows the spectra of the invention-related SPEEK/CF optode (CF immobilized in SPEEK). The spectral position of the emission is shifted towards the shorter wavelengths, compared with the results in solution. A band at 490 nm is prominent in the very acidic pH range. At pH=4 and higher, the emission band at 520 nm appears quite distinctly wherein a shoulder at 550 nm is also formed. With evaluation of the quotients of the intensities at 490 nm and 520 nm, a point of inflection at 4.2 is determined. With evaluation of the quotients of the intensities at 490 nm and 550 nm, a point of inflection at 3.4 is determined. The fraction of the protonated species of the emission at 550 nm is greater than that at 520 nm, which is why the point of inflection lies at smaller pH values.

Figure 6:
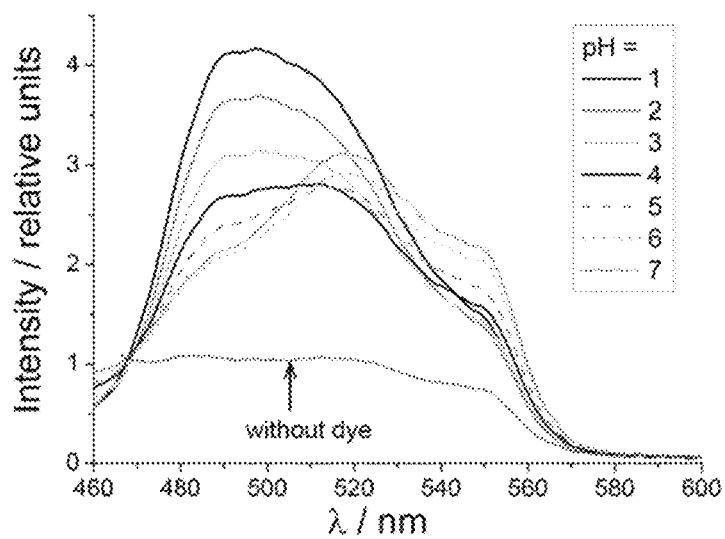
FIG. 6 A shows fluorescence spectra of immobilized CF ($\lambda_{ex}$=405 nm; $\lambda_{em}$=(505–580) nm) in SPEEK at various values of pH.
Figure 6:
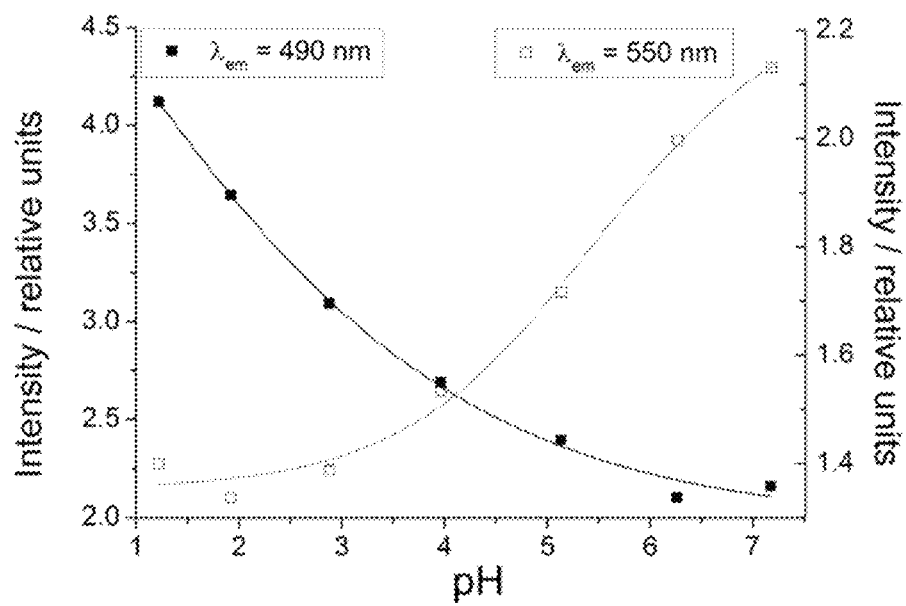

FIG. 6 shows the results of the measurements for excitation at 405 nm. In this, an evaluation at the wavelength 490 nm or 550 nm is possible without referencing as they are well separated. The band shape at the respective pH values corresponds to those with excitation at 440 nm. At 490 nm, the resulting point of inflection is 2, and at 550 nm it is 5.4.

Figure 7:
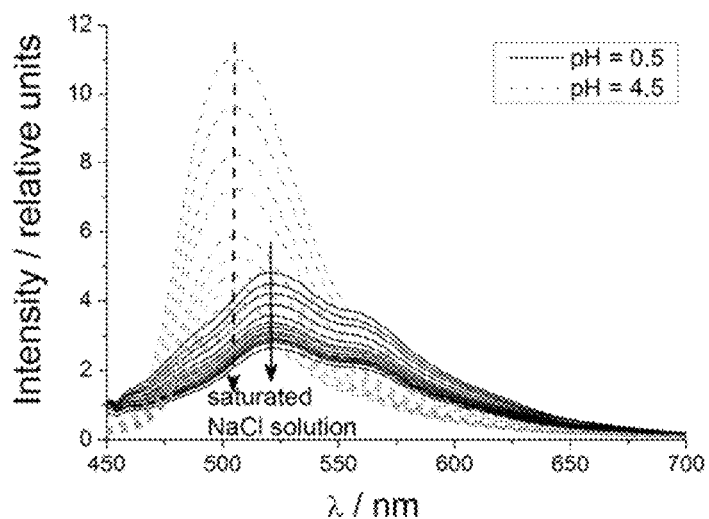
FIG. 7 A shows fluorescence spectra of immobilized CF ($\lambda_{ex}$=440 nm) in SPEEK at pH=0.5 and pH=4.5 for increasing salt concentration.
Figure 7:
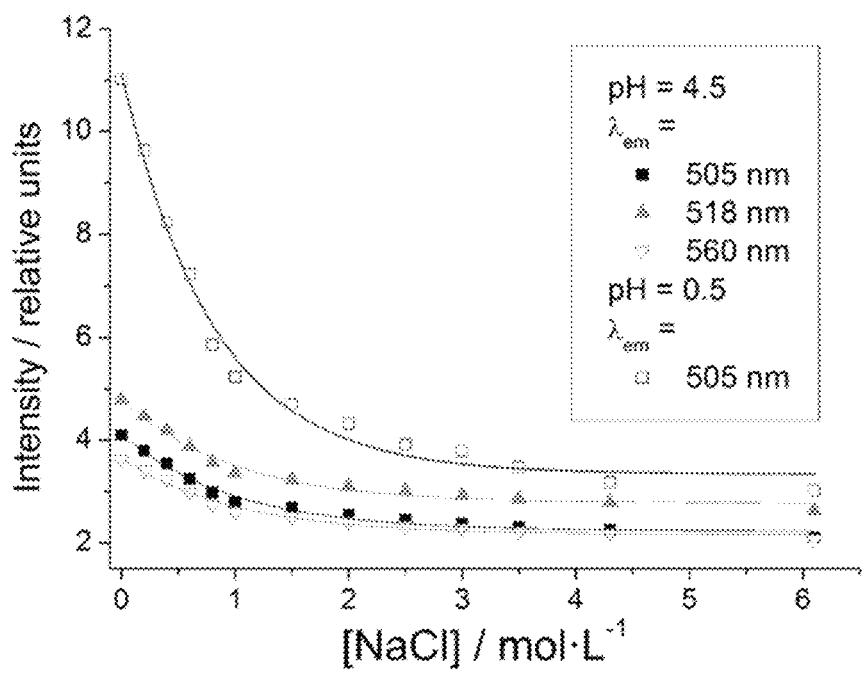
Figure 8:
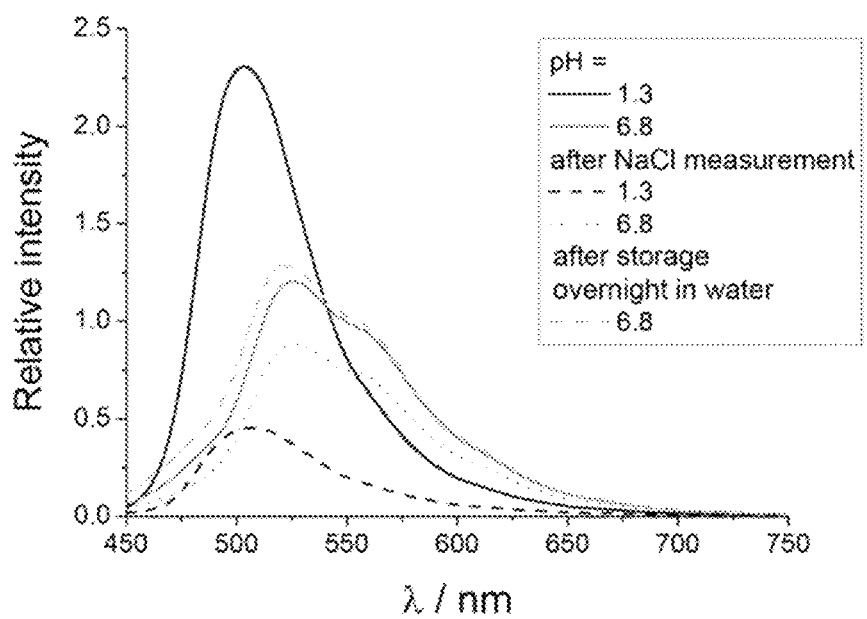
FIG. 8 shows fluorescence spectra of immobilized CF ($\lambda_{ex}$=405 nm) in SPEEK at pH=1.3 and pH=4.5 before and after measurements in the salt concentration.

The salt concentration of the calibration solution has been raised in the measurements shown in FIG. 7. The fluorescence intensity drops with increasing salt concentration, as can be seen in FIG. 7A; the intensity remains constant above 2.5 mol/L NaCl. Because of the internal referencing, a pH-determination should be possible, despite the cross-sensitivity, as the band shape does not change when NaCl is added. At pH=1, only the band at 490 nm appears; the formation of the shoulders at 520 nm and 550 nm remain pH dependent. The falling off of intensity due to salt concentration occurs over the entire wavelength range, which is why only the pH-dependence due to quotient formation is evaluated. FIG. 8 shows that the reduction in intensity is reversed after rinsing and storage in water.

Fluorescence Decay Time-Based Measurements

First, the effect of NaCl on the SPEEK/CF optode material was investigated. This was done for different pH values. A new optical fiber optode was produced for each pH value.

Figure 9:
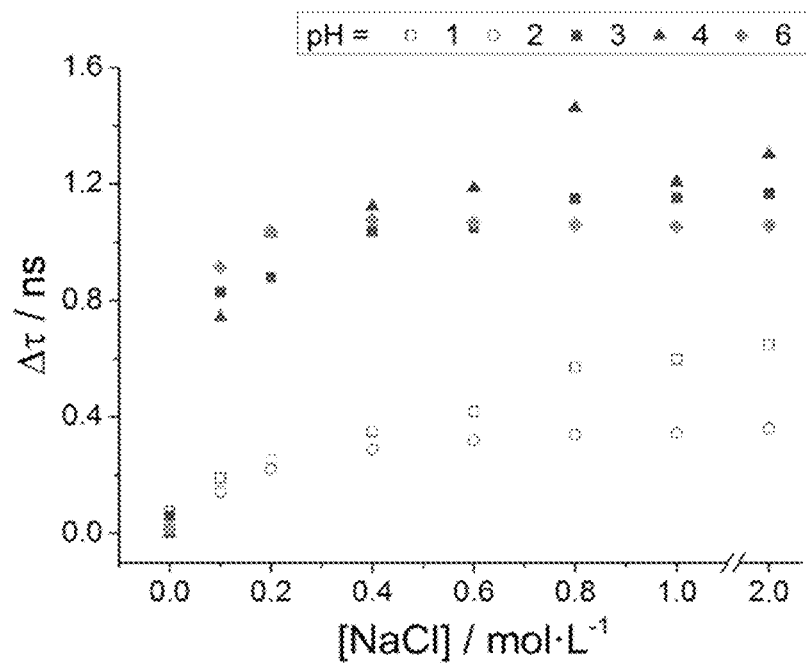
FIG. 9 shows decay times of CF immobilized in SPEEK as a function of NaCl concentration in the solution at various pH values; $\lambda_{ex}$=440 nm.

To indicate the effect of the NaCl concentration, the change in decay time is shown in FIG. 9. It can be seen that the effect of NaCl at pH values less than 3 is smaller than at higher pH values. The decay time increases to a maximum of 1.2 ns. With an NaCl concentration of 0.6 mol/L or more, the decay time remains constant at all pH values. The behavior is, as already observed with TD measurements, not reversible. The decay time of the optodes remains at the longer values, even after storage in deionized water.

Figure 10:
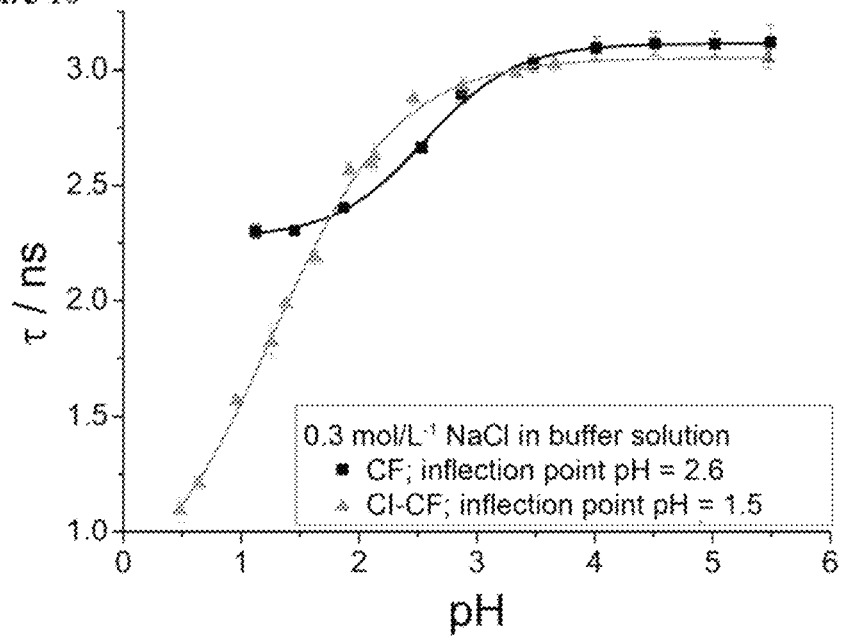
FIG. 10 shows decay times of CF and Cl-CF immobilized in SPEEK as a function of pH; constant NaCl concentration: 0.3 mol/L ($\lambda_{ex}$=405 nm; $\lambda_{em}$=505 nm-580 nm; f=30 MHz)

FIG. 10 shows the results of optical fiber measurements using FD-S at 30 MHz and an excitation wavelength of 405 nm. SPEEK in which CF or Cl-CF has been immobilized was used as optode material. The optode was initially stored in 1 mol/L NaCl solution. NaCl was then added to the buffer solutions in order to get a constant NaCl concentration of 0.3 mol/L in the calibration solutions. The pH value was checked using a glass electrode after salt had been added.

Figure 11A:
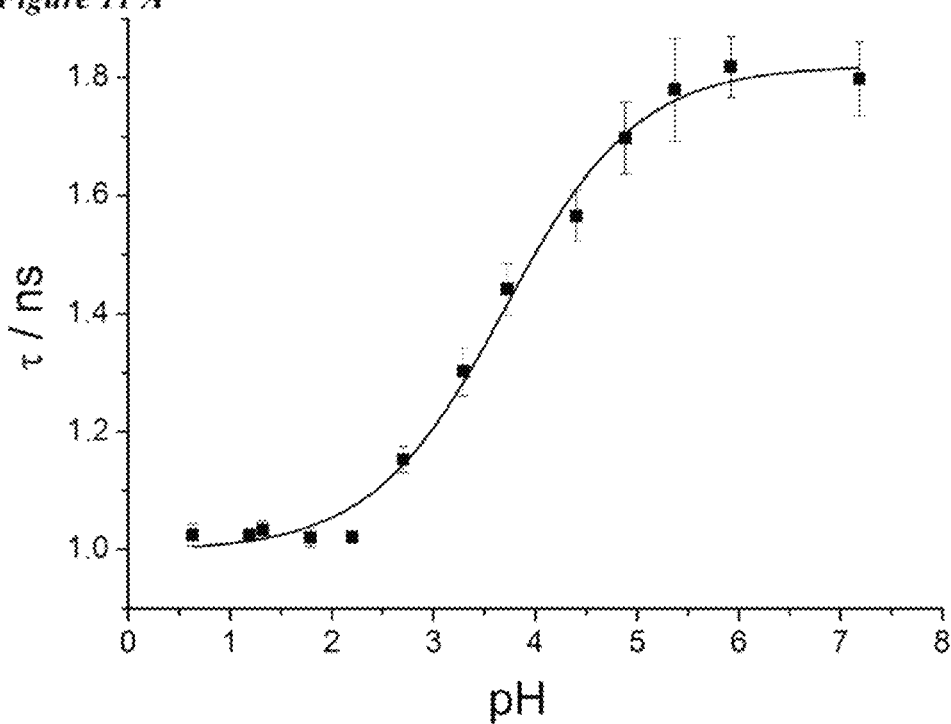
FIG. 11 A shows decay times of CF immobilized in SPEEK as a function of pH, $\lambda_{ex}$=405 nm; $\lambda_{em}$=505 nm-580 nm)
Figure 11:
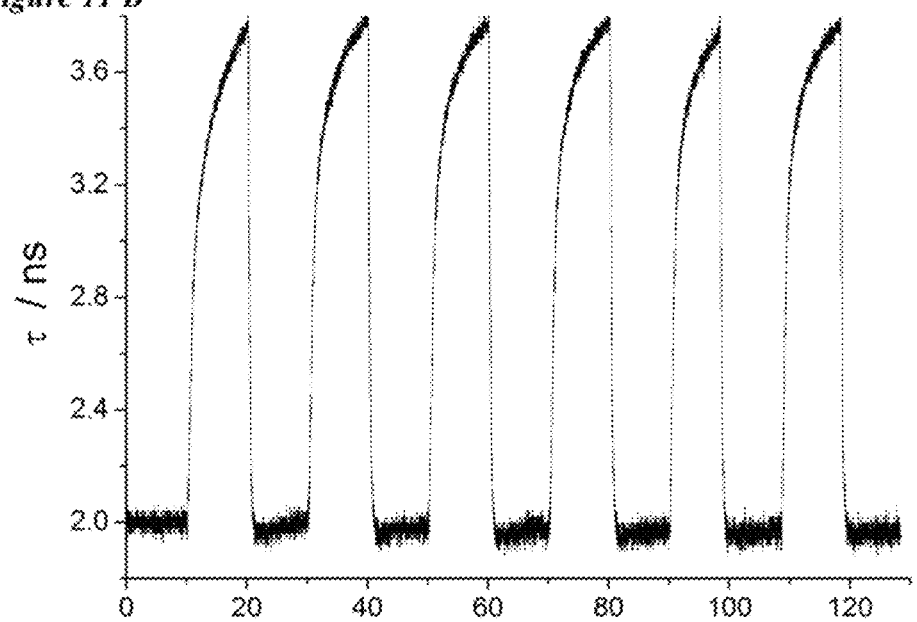

FIG. 11 shows the calibration of a CF/SPEEK optode in buffer solution without increased salt concentration. The decay time was determined three times at each pH value. The point of inflection lies at 3.7±0.2. The measurement with increased salt concentration shows the point of inflection to be at pH=2.6±0.2.

Determining pH Value and Oxygen Concentration with an Invention-Related Optode

The implementation example of the invention-related optode includes the pH-sensitive dye 6-carboxyfluorescein (CF) immobilized in SPEEK. The polymer matrix, used to determine the oxygen concentration, consists of the invention-related optode poly(2,2,2-trifluoroethylmethacrylate (P1) in which Platinum(II)meso-tetra(pentafluorophenyl-porphyrin (Pt-TPFPP) has been immobilized.

Figure 12:
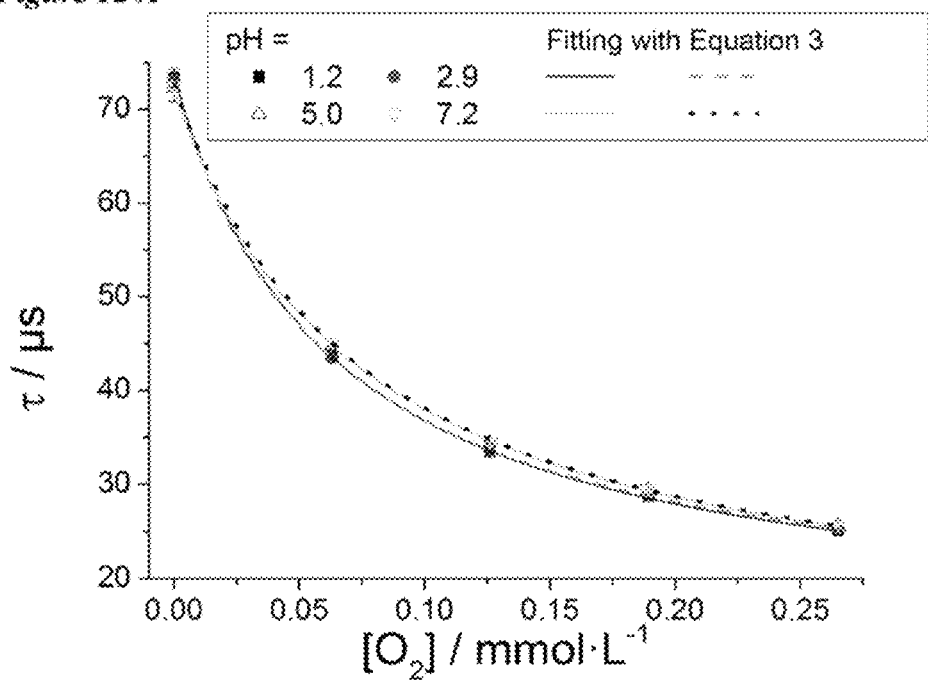
FIG. 12 A shows the decay times of Pt-TPFPP immobilized in P1 as a function of oxygen concentration.
Figure 12:
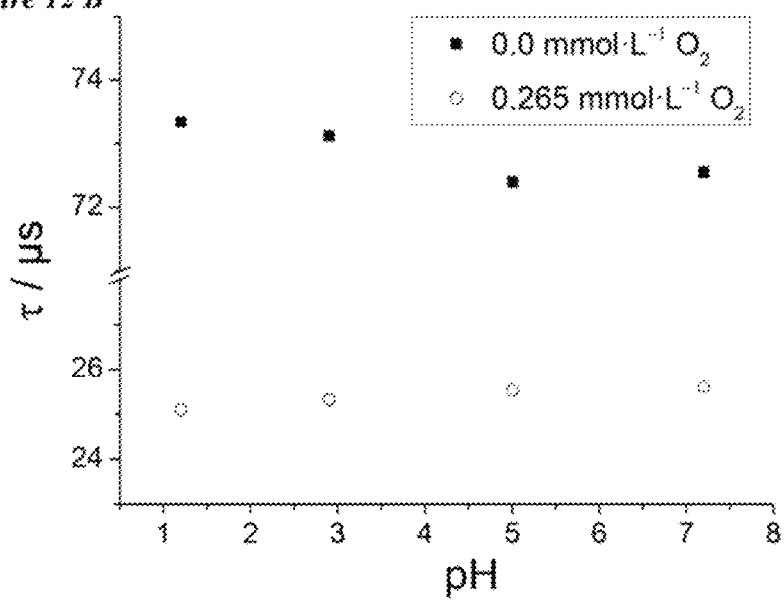

To exclude pH cross-sensitivities, a check was made as to whether the decay time of the optode material for the oxygen determination is dependent on the pH value of the solution. Such a dependence would falsify the measured values. A calibration of the optode for oxygen determination without the pH-sensitive dye in SPEEK was made at various pH values. It should be demonstrated that the decay time of the sensor is independent of the solution pH (FIG. 12).

The Stern-Volmer constant of calibration at various pH values fluctuates between 13 mmol/L and 16 mmol/L; the mean value of all pH values gives a Stern-Volmer constant of (15±2) mmol/L.

For the thick optical fiber used here, the Stern-Volmer constant is somewhat smaller than when using thin fiber tips as the layer thickness of the optode is also greater. The $\tau_0$ value lies between 72.4 µs and 73.4 µs (averaged: 72.8±0.4 µs). The fluctuations in the results when determining the calibration function and using various pH values correspond to the determination at constant pH values. The $O_2$ signal can therefore be assumed as independent of the pH value if the $O_2$ sensitive dye Pt-TPFPP has been immobilized in P1 polymer. There is no cross-sensitivity to the pH value.

The additional pH-sensitive optode material SPEEK containing the immobilized 6-carboxyfluorescein (CF) is now fixed to the fiber coated with the oxygen sensor.

Figure 13:
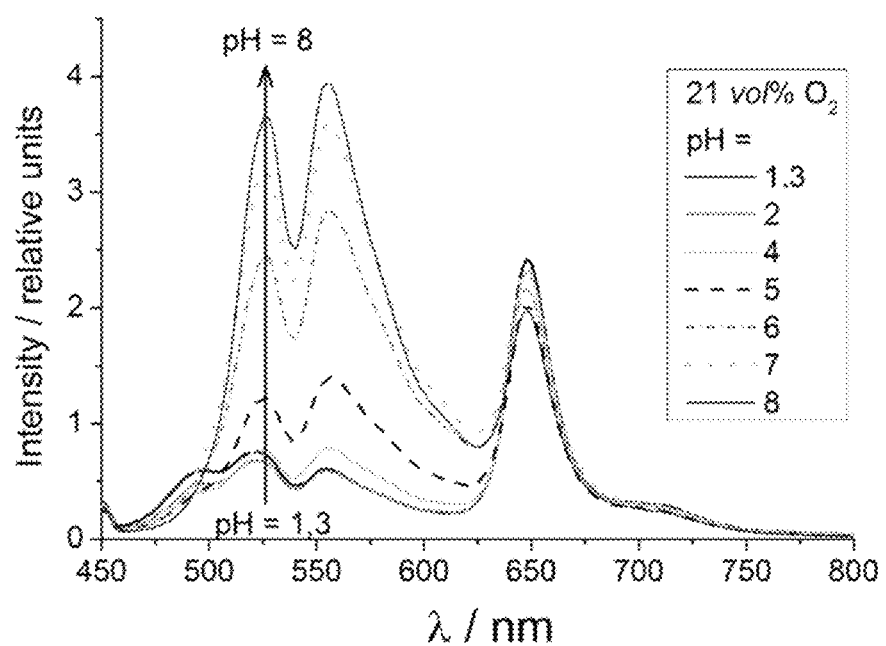
FIG. 13 shows the emission spectra of invention-related CF/SPEEK and Pt-TPFPP/P1 optodes ($\lambda_{ex}$=440 nm)
Figure 13:
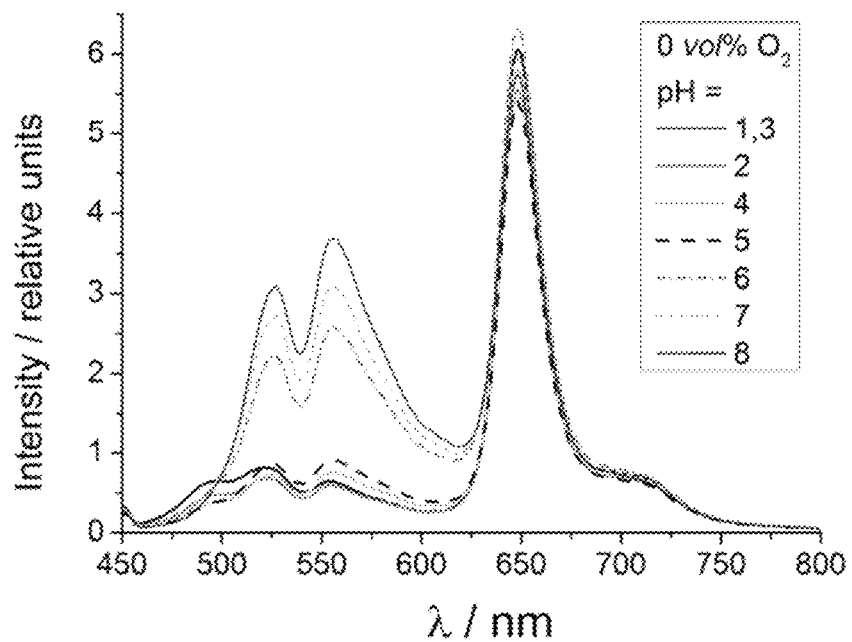
Figure 14:
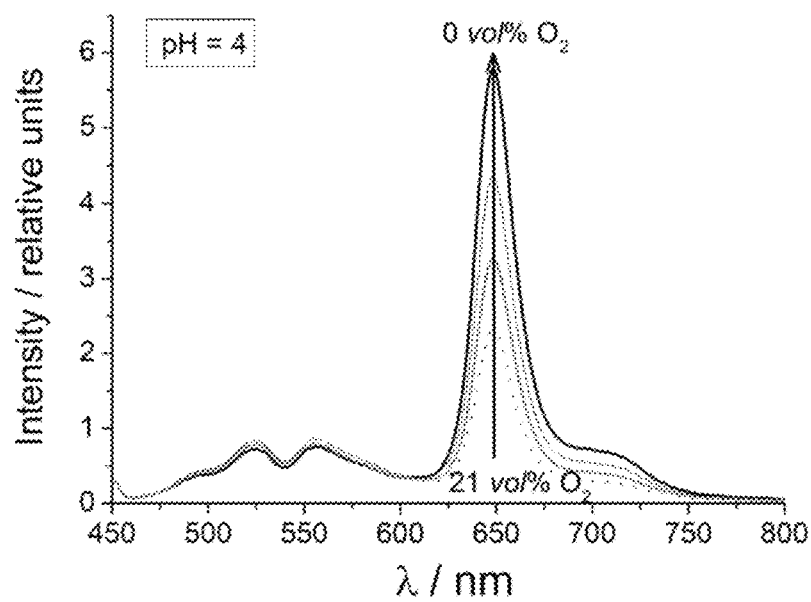
FIG. 14 shows the emission spectra of invention-related CF/SPEEK and Pt-TPFPP/P1 optodes ($\lambda_{ex}$=440 nm)
Figure 14:
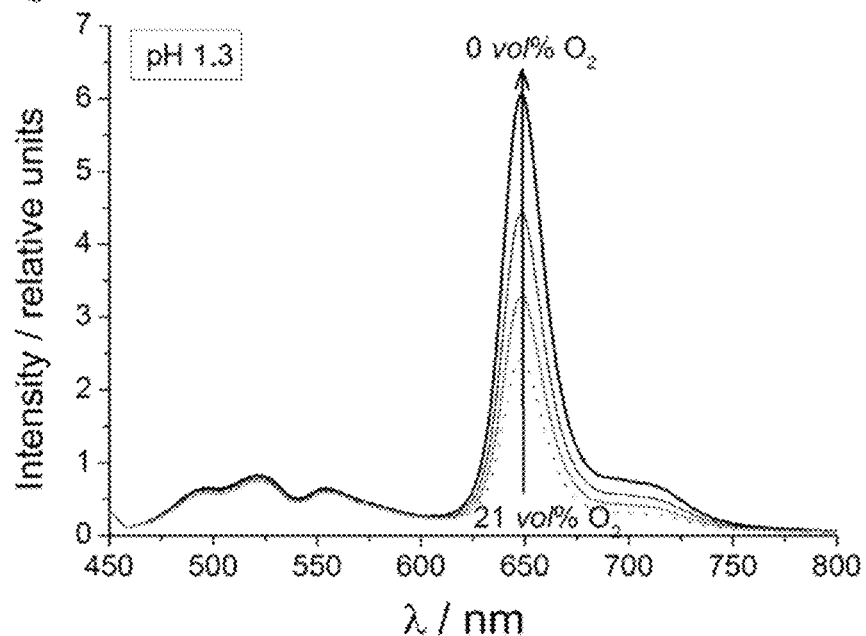

Emission spectra were recorded at different pH values and oxygen concentrations (FIGS. 13 and 14). The spectral positions of the two emissions are well separated from each other in terms of the 440 nm laser diode used for the excitation. This excitation wavelength is more suitable for the CF, which is why the intensities of the two dyes are of the same order.

Figure 15:
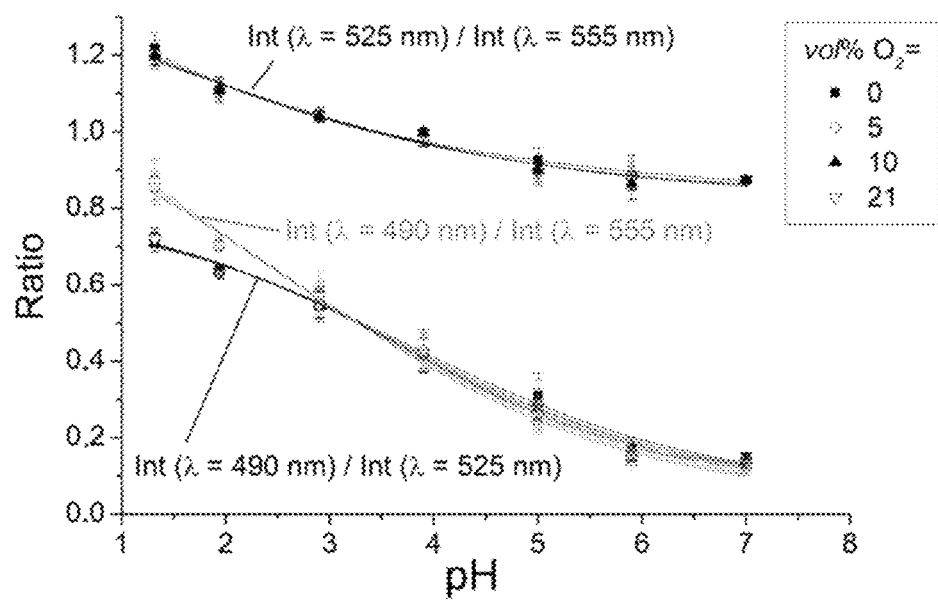
FIG. 15 shows the evaluation of the emission spectra of the invention-related dual-optode for determining pH value and oxygen concentration.

In FIG. 15 A, the ratio of CF signal intensity at different wavelengths is formed and plotted against pH. The evaluation of intensity at $\lambda=490$ nm/$\lambda=555$ nm gives a linear curve between pH=1 and pH=6. The evaluations at $\lambda=490$ nm/$\lambda=525$ nm and $\lambda=525$ nm/$\lambda=555$ nm show a sigmoidal curve with a point of inflection at 3.7±0.4 for all oxygen concentrations. The determination of the pH value is independent of the oxygen concentration in the solution.

In FIG. 15 B, the emission of the Pt-TPFFP at 650 nm is shown with the Stern-Volmer plot that has a linear curve. The gradients of the lines are 5.8±0.2 L/mmol between the pH values 3 and 7 (at pH=1, the gradient is only 5.0±0.2 L/mmol). The immobilization of the $O_2$-sensitive dye in the water-impermeable polymer leads to a negligible dependence of the $O_2$-sensitive dye on pH.

Determining the Decay Times

Figure 16:
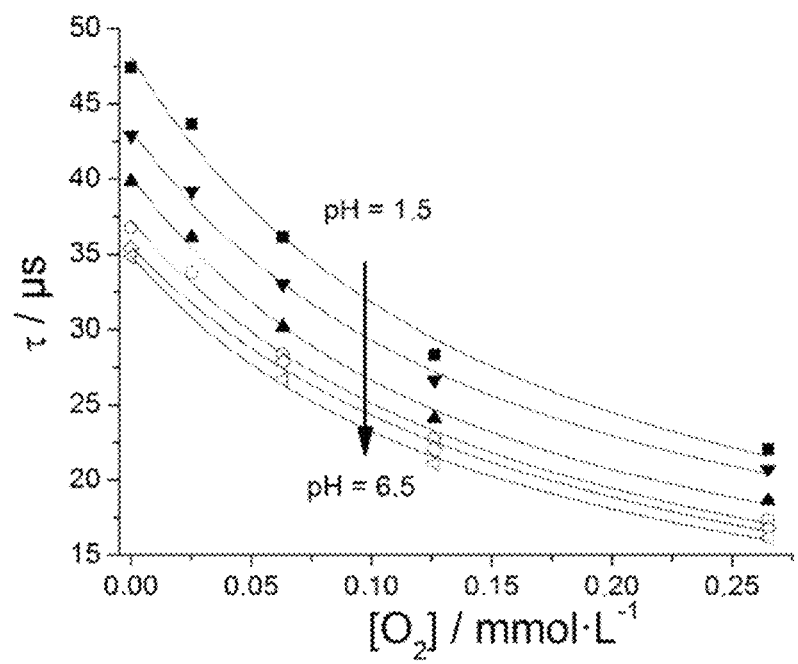
FIG. 16 shows calibrations of the invention-related dual-optode for determining pH value and oxygen concentration.

The decay times of CF and Pt-TPFPP emissions were measured. The 405 nm laser diode used was modulated alternately with 30 MHz (pH sensor) and with the usual frequencies f1=4.5 kHz and f2=9.21 kHz ($O_2$-sensor). FIG. 16 shows the independence of the pH sensor signal from the oxygen concentration. The decay time of the $O_2$-sensitive dye however shows a dependence on pH.

Figure 17:
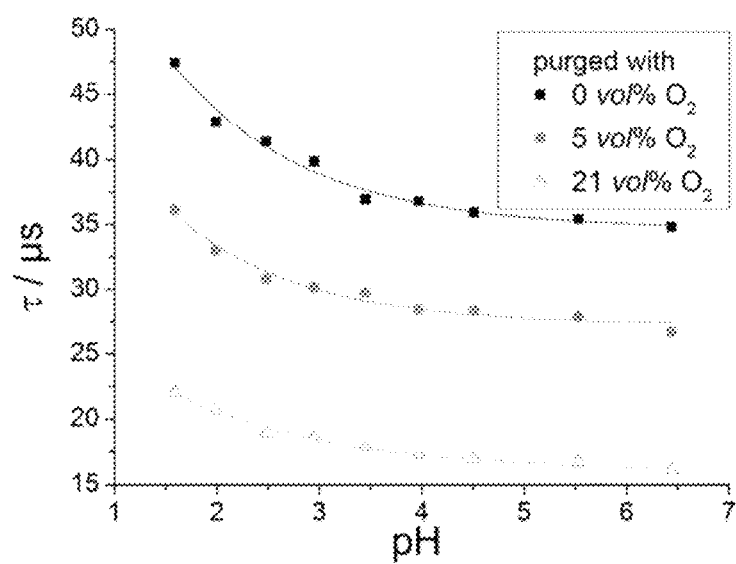
FIG. 17 A shows the decay time of the $O_2$ signal of the invention-related dual-optode for the determination of pH and oxygen concentration as a function of pH at various $O_2$ concentrations.
Figure 17:
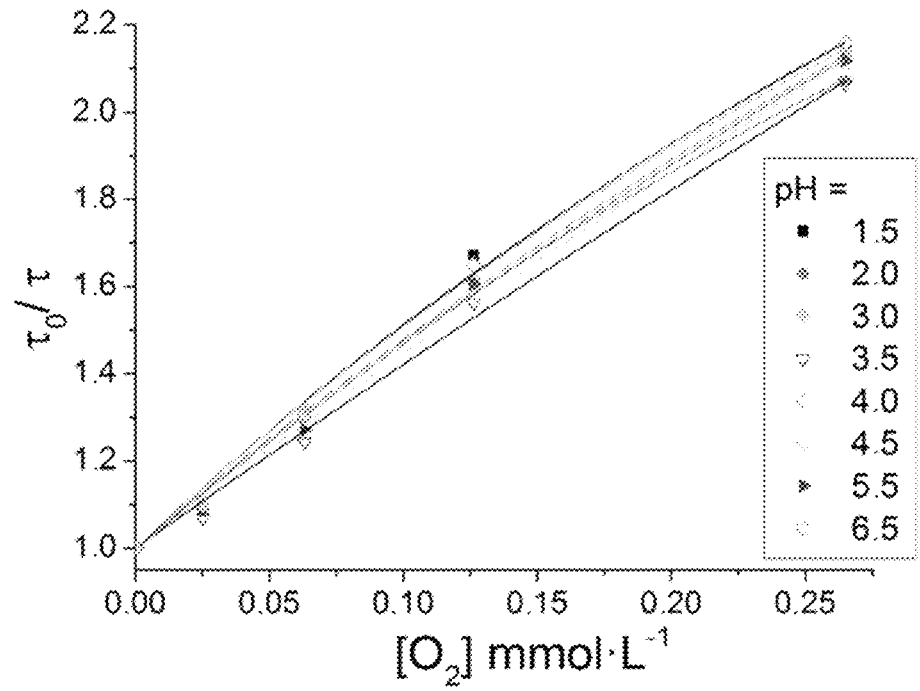

FIG. 17 shows that, at constant oxygen concentration for pH=4 and higher, the decay time of the oxygen signal no longer changes significantly with increase in pH. At and above this pH-value, the intensity of the CF fluorescence also changes only slightly. The decay times of the invention-related dual-optode are shorter than those decay times shown in FIG. 12. The amplitude (intensity) of the background fluorescence, in this case the signal of the pH measurement, is probably not smaller than the actual measurement signal in the red spectral range $\lambda_{em}>600$ nm. The calculated, corrected decay time $\tau\phi$ would therefore have fractions of the short delay time of the CF fluorescence. It can therefore be supposed that the assumption in the corrected decay time from the calculation of the corrected decay time from dual-frequency phase modulation spectroscopy measurements (d-FD-S) is not fulfilled, i.e. the amplitude of the background fluorescence, and with that $\tau_2$, is not to be ignored and therefore the calculated, corrected decay time of the $O_2$ signal appears shorter. An improvement can be achieved by the use of even more efficient bandpass filters, which also absorb a part of the Pt-TPFPP emission but compensate for that by holding back any CF emission from the $O_2$ detector. The filter for this must only become transparent above $\lambda=650$ nm.

FIG. 17 B shows the Stern-Volmer plot of the invention-related dual-optode for determining pH and oxygen concentration. For each pH value, the correspondingly measured $\tau_0$-value was used for the calculation of the ratio. A direct correlation between the pH value and the $O_2$ concentration is not observed. The mean $K_{SV}$ value for all pH values has a value of 6.0 L/mmol with an error of 0.8 L/mmol, the p value is calculated as 0.87±0.04.

The results of the tests with the dual-optode show that, for each sensor, in practice, the $\tau_0$ values for at least three pH values (2; 3; 6) and then two further oxygen concentrations (10 vol %; 21 vol %) at one of the three pH values, must be calibrated. Before the measurements can be carried out on the sample, six different calibration solutions are therefore measured. As the determination of the pH value is not dependent on the oxygen concentration, the pH of the sample is determined first in order to calculate the correct $\tau_0$ value of the $O_2$ signal for the calibration function in calculating the oxygen concentration.

To summarize, an invention-related optode was produced which enables the measurement of pH using the decay time of the sensor dye. In a further implementation example, an optode was provided with which pH and oxygen concentration can be determined via the decay time of the sensor dyes used. In this, the possibility always exists, via the decay time determination, of performing a signal separation as the pH sensor is determined from the change in fluorescence and the $O_2$ sensor via the measurement of the much slower decaying phosphorescence.

The measurements presented were all performed using a triple fiber with different detectors. The optode materials were deposited on one fiber tip. The separation of the signals takes place in the frequency domain and in the spectral position of the two sensor dyes. The pH measurement shows no dependence on oxygen concentration, shows however the decay time of the $O_2$ determination—a signal that is dependent on the pH value.

This dependence can be neglected for the evaluation by applying the Stern-Volmer relationship and the associated standardization with the decay time without quencher addition. This decay time $\tau_0$ must however be determined for as many pH values as possible during the calibration to be able to perform a precise determination of the $O_2$ concentration. Because of the good spectral separation of the two signals, CF and Pt-TPFPP, a determination of the two parameters using this form of implementation of the invention-related optode by stationary methods is also possible. In the case of applications involving complex matrices, however, the determination using the decay time measurement method should be preferred, as effects of background signals (e.g. auto-fluorescence of the components in the sample or illumination light) can be corrected.

The optical determination of the pH value is achieved for example with the invention-related CF/SPEEK optode in the acidic pH range, the application of FD-S, TD-S and also using stationary measurements.

The washing-out effect observed initially was minimized by heat treatment (storage in 65° C.—hot solution for 12 hours), whereby one sensor can be used for a period of several days to weeks without loss of dye in the matrix due to the wash-out effects. The emission spectra of the CF/SPEEK optode showed no changes during increase in temperature (5° C.<θ<70° C.). Because of the immobilization of the CF, the non-radiative deactivation is minimized as the molecule is securely fixed in the matrix, which is why a 50% reduction in fluorescence intensity was observed—not like the case with the measurements in solution.

Determination of Chloride Ion Concentration, Oxygen Concentration and pH Using the Invention-Related Optode pH-CF/SPEEK-(Pt-TPFPP)/P1-Lucigenin/PHPMA The optode for determining pH value and oxygen concentration was suppl-mented by a sensor material for determining the chloride ion concentration. Lucigenin that has been immobilized in poly(2-hydroxypropylmethacrylate) (PHPMA) is used. The simultaneous measurement of pH value and oxygen concentration with the invention-related dual-optode has already been explained above in detail.

The chloride ion-sensitive dye Lucigenin was immobilized in PHPMA and chloride concentration was determined using TD-S.

Figure 19:
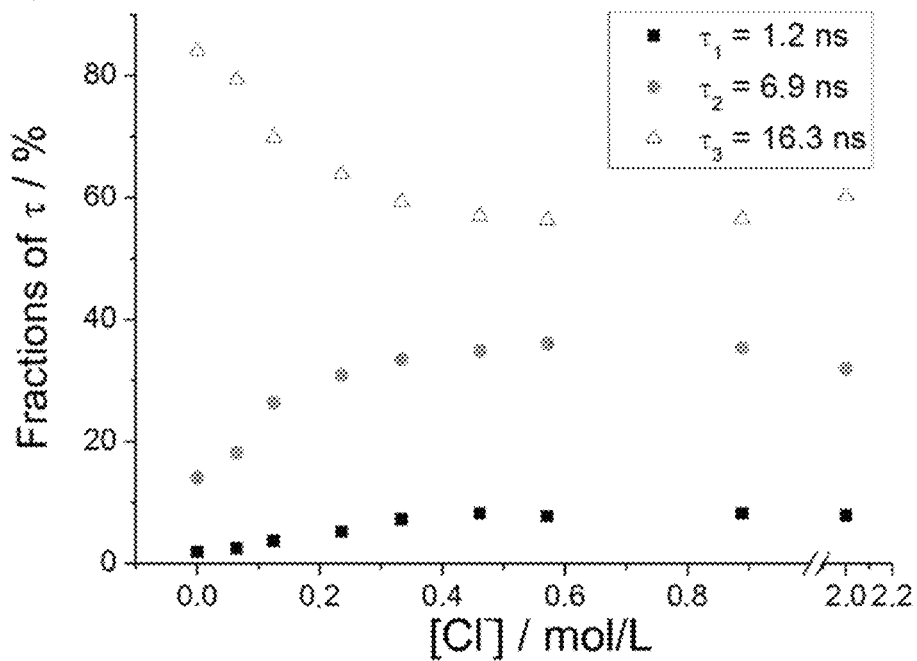
FIG. 19 shows the determination of chloride ion concentration by means of TD-S when using the Lucigenin/PHPMA optode.
Figure 19:
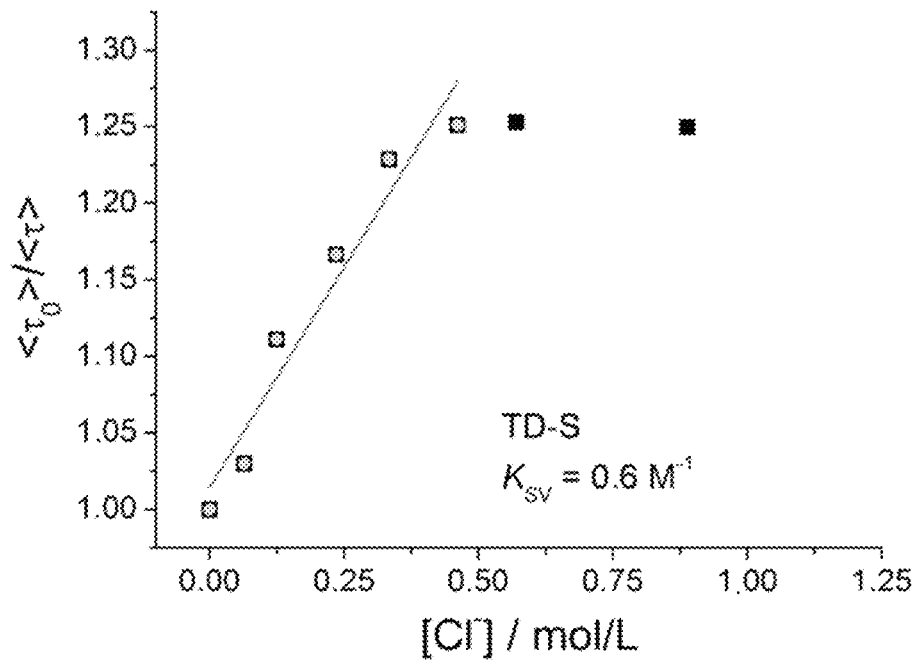

This optode material can, for example, be applied directly with the oxygen sensor Pt-TPFPP/P1 P to a fiber tip as superposition does not occur, neither spectrally nor in the time domain. The simultaneous determination of pH, chloride ion concentration and oxygen concentration is possible when performing this at several modulation frequencies in the MHz and kHz ranges. In FIG. 19 shows the determination of chloride ion concentrations using a Lucigenin/PHPMA optode. FIG. 20 shows the Stern-Volmer plot.

The Following Arrangements and Devices were Used in the Investigations Performed:

Absorption and Fluorescence Spectroscopy

Measurements of absorption spectra took place using a dual-beam spectrometer (Perkin Elmer Lambda 750 UV-Vis Spectrophotometer). The stationary fluorescence spectra were recorded using a FluoroMax3-P (Jobin Yvon Horiba). For reference measurements related to phase modulation spectroscopy, time-resolved measurements were performed with a Fluoromax4 (Jobin Yvon Horiba) in the TCSPC or MCS mode. TD-S measurements were also performed with a fluorescence spectrometer (Edinburgh Instruments FLS920). For the TD-S measurements with optical fibers, the signal was recorded by the WaveRunner 104MXi-A oscilloscope from LeCroy. The excitation was generated by a 405 nm emitting laser diode (L, NICHIA NDV4313), which was pulsed by a function generator (Tektronix AFG 3102). Work in the context of the invention was also performed using the fiber spectrometer (ALS Co. SEC2000 Spectra System). For absorption measurements, the intensity is measured with an integral white-light source as reference spectrum before beginning the actual measurement. The intensity at different wavelengths is recorded on the CCD chip in a single measurement in which a spectrum over the entire spectral range from 250 nm to 900 nm can be measured. The spectrometer was operated in the absorption and fluorescence modes. To attenuate the excitations signal when recording fluorescence spectra, a long-pass filter (cut-off wavelength at 450 nm Thorlabs FEL0450) was placed in front of the detector. A 450 nm laser diode (NICHIA NDB7875) or the 405 nm laser diode mentioned above supplied the excitation.

Phase Modulation Spectroscopy

Modulation in the kHz Range

For the oxygen sensor with the dye Pt-TPFPP, the frequency of 9.24 kHz from a function generator (ELV-MFG 9001 M) was coupled into a dual-channel, lock-in amplifier (EG&G Instruments) which superposes this with a frequency of 4.6 kHz. A 405 nm laser diode (NICHIA NDV4313) is then supplied via the modulation of the power supply of a laser driver (Stanford Research System LDC501) with these two frequencies. The laser diode (LD) and the avalanche photo diode (APD) are built into a triplexer (manufactured by Optricon in cooperation with the physical chemistry department of Potsdam University). Both the intensity-modulated excitation light and the emission signal are coupled into the fiber within the triplexer or led from the fiber to the APD.

The sensor signal is led via a dichroic beam splitter (BS, transparent to blue excitation light, reflects the red emission signal) and after passing through an additional bandpass filter (BP; Semrock BrightLine R Fluorescence 607/70) and then led to an avalanche photo diode (APD). The current measured is increased in the RF amplifier from FEMTO (DCPCA 20) and then the phase shift relative to the excitation light determined in the lock-in amplifier. The data analysis is performed using a Visual Basic-based program (developed by Dr. E. Schmalzlin in the Physical Chemistry department of Potsdam University), which calculates the decay time and oxygen concentration. In the Opal system used (Colibri Photonics GmbH), the frequency generator and the lock-in amplifier are integrated into a single unit. This makes it easier to transport. In the further development of the Opal system, Opal2, all electronic and optical components (triplexer) required are combined into one portable device.

Modulation in the MHz Range

The construction principle is similar to that used for the oxygen sensor, but the devices used operate in the MHz range. Here, work is done at only one modulation frequency, which is why the dual-channel, lock-in amplifier without dual-reference function (Stanford Research Systems SR844) was used. The frequency of 30 MHz (if not otherwise stated) is coupled to a function generator (Tektronix AFG 3102) as reference, also to laser driver (ELOVIS (electronics-optics-solutions), DynaLase-C system).

The intensity modulation of a 405 nm LD (NICHIA NDV4313) or of a 450 nm (NICHIA NDB7875) or 470 nm LD (NICHIA NDA4611E) was achieved by modulating the current level produced by the laser driver. The emission signal is detected by a photomultiplier (Hamamatsu H6780-20) and amplified using an RF amplifier (FEMTO DHPCA-100). The separation of the excitation light is done by means of bandpass filter from Semrock (BrightLine R fluorescence filter 550/88). The lock-in amplifier was read-out using a Labview-based software.

Modulation in Two Frequency Ranges: Dual-Optode SPEEK/CF-Pt-TPFPP/P1

Figure 18:
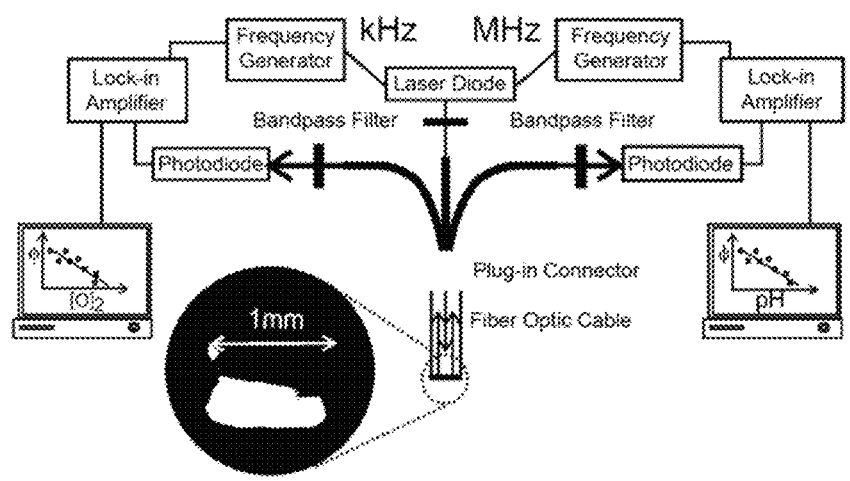
FIG. 18 shows the schematic set-up for the spatially resolved determination of pH values (right half of the diagram) and oxygen concentrations (left half of the diagram); also shown is a microscope image of the invention-related dual-optode when excited using UV light, taken with a 500 nm longpass filter.

As shown in FIG. 18, a 405 nm laser diode was modulated alternately at 30 MHz and 9.24/4.62 kHz. The excitation light was coupled into a fiber (430 μm diameter) and fed into a 1 mm fiber via a plug-in connector. Both the pH optode material and the oxygen-sensitive optode material were attached to its tip. The emission signal was led via two 430 μm fibers to the relevant detectors. For the oxygen determination, the triplexer was first used—as described above for several measurements by the Hamamatsu-PMT (H10723-20) with, placed in front of it, filters from Semrock (BrightLine R fluorescence filter 607/70 for Ru-based dye; BrightLine R FF01-635/LP-25 for Pt-based and BrightLine R FF01-675/67-25 for Pd-based dye).

The invention claimed is:

1. An optode for the determining of chemical parameters of a sample,
   characterized in that the optode consists of a polymer matrix that in turn consists of a sulfonated polyether ether ketone (SPEEK) in which a sensor dye is immobilized or several sensor dyes are immobilized, wherein at least one of the immobilized sensor dyes is pH-sensitive.

2. The optode according to claim 1, characterized in that at least one further sensor dye is immobilized in the sulfonated polyether ether ketone (SPEEK).

3. The optode according to claim 1, characterized in that it consists of at least one further polymer matrix, in which at least one further sensor dye is immobilized.

4. The optode according to claim 2, characterized in that the at least one further sensor dye is selected from oxygen-sensitive, halide ion-sensitive, sodium ion-sensitive, potassium ion-sensitive, pH-sensitive and calcium ion-sensitive dyes.

5. The optode according to claim 1, characterized in that the pH-sensitive sensor dye is selected from
   4-{4[4-(dipentylamino)phenyl]-1,3-butadienyl}-1-(4-sulfobutyl)pyridinium hydroxide (RH421, bis-(1,3-dibutylbarbituric acid)trimethineoxonol ($Dibac_4(3)$), 6-carboxyfluorescein (CF) , and 5(6)-carboxy-2',7'- dichlorofluorescein (Cl-CF) and 8-hydroxy-1,3,6-pyrenetrisulfonic acid-trisodium salt (HPTS).

6. The optode according to claim 1, characterized in that the oxygen-sensitive dye is selected from Pt (II) meso-tetra (pentafluorophenyl)porphyrin (Pt-TPFPP), Pd(II)meso-tetra (pentafluorophenyl)porphyrin, Ruthenium(II)-tris(4,7-diphenyl-1,10-phenanthroline)-perchlorate (Ru-pCl) and ruthenium(II)-tris(4,7-diphenyl-1,10-phenanthroline)dichloride;

the halide-sensitive dye is selected from the chloride ion-sensitive dyes N,N'-dimethyl-9, 9'-bisacridiniumnitrate (Lucigenin), 6-methoxy-N-(3-sulfopropyl)quinolinium (SPQ), and N-(ethoxycarbonylmethyl)-6-methoxyquinolinium bromide (MQAE);

the sodium ion-sensitive dye is selected from N,N'-[1,4,10-trioxa-7,13-diazacyclopentadecane-7,13-diylbis(2,5-dimethoxy-4,1-phenylene)]bis[3',6'-bis(acetyloxy)-2',7'-dichloro-3-oxo-spiro[isobenzofuran-1(3H),9'[9H]xanthen]-5-carboxamide, (Sodium Green ®) and N-(4-[1-(7-diethylaminocoumarin-3-yl)-1H-1,2,3-triazol-4yl]phenylaza-18-crown-6-ether;

the potassium ion-sensitive dye is N-(2-methoxyethoxy)phenylaza-18-crown-6)-4-(coumarinyl)-1H-1,2,3-triazol, the calcium ion-sensitive dye selected is from N-[2-[(acetyloxy)methoxy]-2-oxoethyl]-N-4-[[[3',6'-bis(acetyloxy)-2',7'-difluoro-3-oxospiro[isobenzofuran-1(3H),9'-[9H]xanthen]-5-yl]carbonyl]amino]-2-[2-[2-[bis[2-[(acetyloxy)methoxy]-2-oxoethyl]amino]phenoxy]ethoxy]phenyl]-glycine-(acetyloxy)methyl ester (Oregon Green ™ 488 BAPTA-1), N-[2-[2-[2-[bis(carboxymethyl)amino]-5-[[(2',7'-difluoro-3',6'-dihydroxy-3-oxospiro[isobenzofuran-1(3H),9'-[9H]xanthen]-5-yl)carbonyl]amino]phenoxy]ethoxy]-6-fluorophenyl]-N-(carboxymethyl)-glycine-hexapotassium salt (Oregon Green™ 488 BAPTA-6F) and N-[2-[2-[2-[bis(carboxymethyl)amino]-5-[[(2',7'-difluoro-3',6'-dihydroxy-3-oxospiro[isobenzofuran-1(3H),9'-[9H]xanthen]-5-yl)carbonyl]amino]phenoxy]ethoxy]-5-nitrophenyl]-N-(carboxymethyl)-glycine-hexapotassium salt (Oregon Green™ 488 BAPTA-5N).

7. The optode according to claim 3, characterized such that the polymer of at least one further polymer matrix selected is of poly(2,2,2-trifluoroethylmethacrylate (P1), poly(2-hydroxypropylmethacrylate) (PHPMA), poly(2-hydroxyethylmethacrylate) (PHEMA), polyurethane (PU), polyvinylpyrrolidone (PVP), poly(1-vinylpyrrolidone)-co-styrene (PVPS), polyvinylchloride (PVC), polyacrylonitrile-polyacrylamide-blockcopolymer (HYPAN HN 80) and polystyrene.

8. The optode according to claim 1, characterized in that the pH-sensitive dye is 6-carboxyfluorescein (CF) or 5(6)-carboxy-2',7'-dichlorofluorescein (Cl-CF), the further polymer matrix is a poly(2,2,2-trifluoroethylmethacrylate) matrix and the oxygen-sensitive dye is Pt(II)meso-tetra (pentafluorophenyl)porphyrin or Pd(II)meso -Tetra(pentafluorophenyl)porphyrin.

9. The optode according to claim 3, characterized in that the optode comprises two polymer matrices, wherein the first additional polymer matrix consists of the polymer poly(2-hydroxypropylmethacrylate), in which the chloride ion-sensitive dye N,N'-dimethyl-9,9'-bisacridiniumnitrate is immobilized, and the second further polymer matrix consists of the polymer poly(2,2,2-trifluoroethylmethacrylate), in which the oxygen-sensitive dye Pt(II)meso-tetra(pentafluorophenyl)porphyrin (Pt-TPFPP) or Pd(II)meso-Tetra(pentafluorophenyl)porphyrin (Pd-TPFPP) is immobilized.

10. The optode according to claim 1, characterized in that on the polymer layer, in which the sensor dye is immobilized, or between the further polymer layers in which one or more sensor dyes are immobilized, a further layer or several further layers are applied, wherein no sensor dye is immobilized in these one or more separation layers.

11. The optode according to claim 1, characterized in that the optode includes at least one substrate on which one or several polymer matrices, and the sensor dyes immobilized there, are fixed.

12. The optode according to claim 11, characterized in that it is at least one substrate is selected from glass substrates or polymer substrates.

13. The optode according to claim 11, characterized in that the substrate consists of a polymer matrix, in which a sensor dye is immobilized.

14. The optode according to claim 1, characterized in that it is connected with one or more optical fibers or part of an optical fiber.

15. A method for determining the pH of a sample, the method comprising the steps of:
    a) providing a pH-sensitive optode according to claim 1;
    b) inserting the pH-sensitive optode into the sample;
    c) conducting excitation light into the sample;
    d) measuring the emission fluorescence of the sample; and
    e) determining the pH of the sample based on the measured emission fluorescence.

16. A method for determining the pH and at least one of carbon dioxide concentration and ammonia concentration and oxygen concentration and halide ion concentration and sodium ion concentration and potassium ion concentration and calcium ion concentration of a sample, the method comprising the steps of:
    a) providing a pH-sensitive and additionally at least one of carbon dioxide-sensitive and ammonia-sensitive and oxygen-sensitive and halide ion-sensitive and sodium ion-sensitive and potassium ion-sensitive and calcium ion-sensitive optode according to claim 1;
    b) inserting said optode into the sample;
    c) conducting excitation light into the sample;
    d) simultaneously or time-shifted measuring the emission fluorescence of the sample; and
    e) determining the pH and the at least one of carbon dioxide, ammonia, oxygen, halide ion, sodium ion, potassium ion, and calcium ion concentration of the sample based on the measured emission fluorescence.

17. The method according to claim 15, characterized in that measuring of the emission fluorescence in step d) is performed stationary or time-resolved using a microscope, CCD camera, reflection spectroscopy, fluorescence spectroscopy, time-domain spectroscopy and/or phase modulation spectroscopy.

18. The method according to claim 16, characterized in that measuring of the emission fluorescence in step d) is performed stationary or time-resolved using a microscope, CCD camera, reflection spectroscopy, fluorescence spectroscopy, time-domain spectroscopy and/or phase modulation spectroscopy.

* * * * *